United States Patent
Li

(10) Patent No.: US 7,179,595 B2
(45) Date of Patent: Feb. 20, 2007

(54) COMPOSITIONS AND METHODS FOR GENERATING ANTIGEN-BINDING UNITS

(75) Inventor: Shengfeng Li, 1114 Ladera Way, Belmont, CA (US) 94003

(73) Assignee: Shengfeng Li, Belmont, CA (US)

( * ) Notice: Subject to any disclaimer, the term of this patent is extended or adjusted under 35 U.S.C. 154(b) by 0 days.

(21) Appl. No.: 10/226,949

(22) Filed: Aug. 22, 2002

(65) Prior Publication Data

US 2004/0265901 A1    Dec. 30, 2004

Related U.S. Application Data

(60) Provisional application No. 60/314,489, filed on Aug. 22, 2001.

(51) Int. Cl.
    *C12Q 1/68* (2006.01)
(52) U.S. Cl. .............. 435/6; 435/5; 435/7.1; 435/69.6; 435/69.7; 435/254.2; 435/320.1; 435/325; 435/465; 530/350; 530/371; 530/387.3; 530/388.22; 530/388.75; 536/23.1; 536/23.2; 536/23.4; 536/23.5; 536/241
(58) Field of Classification Search .............. 435/5, 435/6, 7.1, 69.6, 69.7, 254.2, 320.1, 325, 435/465; 530/350, 371, 387.3, 388.22, 388.75; 536/23.1, 23.2, 23.4, 23.5, 24.1
See application file for complete search history.

(56) References Cited

U.S. PATENT DOCUMENTS

| | | | |
|---|---|---|---|
| 5,270,202 A | 12/1993 | Raychaudhuri et al. | 435/327 |
| 5,405,783 A | 4/1995 | Pirrung et al. | 436/581 |
| 5,412,087 A | 5/1995 | McGall et al. | 536/24.3 |
| 5,445,934 A | 8/1995 | Fodor et al. | 435/6 |
| 5,695,937 A | 12/1997 | Kinzler et al. | 435/6 |
| 5,932,448 A * | 8/1999 | Tso et al. | 435/69.6 |
| 5,955,280 A * | 9/1999 | Vidal et al. | 435/6 |
| 6,248,516 B1 | 6/2001 | Winter et al. | 435/6 |
| 6,406,863 B1 * | 6/2002 | Zhu et al. | 435/7.1 |
| 6,504,008 B1 * | 1/2003 | Xu et al. | 530/350 |
| 6,777,235 B1 * | 8/2004 | Ong et al. | 435/455 |
| 6,833,441 B2 | 12/2004 | Wang et al. | |

FOREIGN PATENT DOCUMENTS

| | | |
|---|---|---|
| EP | 0699755 | 3/1996 |
| WO | WO 93/15210 | 8/1993 |

OTHER PUBLICATIONS

Ardnt et al., "Helix-stabilized Fv (hsFv) Antibody Fragemnts: Substituting the Constant Domains of a Fab Fragment for a Heterodimeric Coiled-coil Domain," *J. Mol. Biol.* (2001) 312:221-228.

Visintin, et al., (1999) "Selection of Antibodies for Intracellular Function Using a Two-Hybrid *In Vivo* System" *Proc. Natl. Acad. Sci.* 96(21):11723-11728.

Ausubel, et al., eds., (1987) "Current Protocols in Molecular Biology" [Table of Contents Provided].

Brinkman, et al., (1992) "A Recombinant Immunotoxin Containing a Disulfide-Stabilized Fv Fragment" *Proc. Natl. Acad. Sci. USA* 90(16):7538-7542.

Cohen, et al., (1989) "The Product of a *Fos*-Related Gene, *Fra*-1, Binds Cooperatively to the AP-1 Site with Jun: Transcription Factor AP-1 is Comprised of Multiple Protein Complexes" *Genes & Dev.* 3:173-184.

Freshney, ed., (1987) "Animal Cell Culture" [Table of Contents Provided].

Gentz, et al., (1992) "Parallel Association of Fos and Jun Leucine Zippers Juxtaposes DNA Binding Domains" *Science* 243:1695-1699.

Glaser, et al., (1992) "Dissection of the Combining Site in a Humanized Anti-Tac Antibody" *J. Immunol.* 149:2607-2614.

Glockshuber, et al., (1990) "A Comparison of Strategies to Stabilize Immunoglobulin $F_v$ Fragments" *Biochemistry* 29:1362-1367.

Harlow & Lane, eds., (1988) "Antibodies, A Laboratory Manual" [Table of Contents Provided].

Huston, et al., (1988) "Protein Engineering of Antibody Binding Sites: Recovery of Specific Activity in an Anti-Digoxin Single-Chain Fv Analogue Produced in *Escherichia coli*" *Proc. Natl. Acad. Sci. USA*, 85(16):5879-5883.

Larrick, et al., (1989) "Rapid Cloning of Rearranged Immunoglobulin Genes from Human Hybridoma Cells Using Mixed Primers and the Polymerase Chain Reaction" *Biochem. Biophys. Res. Commun.* 160:1250-1255.

Levitt, et al., (1983) "Molecular Dynamics of Native Protein" *J. Mol. Biol.* 168:595-620.

Matthews, ed., (1991) "Plant Virology" 3rd Edition [Table of Contents Provided].

McPherson, Hames & Taylor, eds., (1995) "PCR 2: A Practical Approach" [Table of Contents Provided].

Miltenyi, et al. (1990) High Gradient Magnetic Cell Separation with MACS[1] *Cytometry* 11:231-238.

Nakabeppu, et al., (1988) "DNA Binding Activities of Three Murine Jun Proteins: Stimulation by Fos" *Cell* 55:907-915.

(Continued)

*Primary Examiner*—Larry R. Helms
*Assistant Examiner*—Parithosh K. Tungaturthi
(74) *Attorney, Agent, or Firm*—Morgan Lewis & Bocklus LLP

(57) ABSTRACT

The present invention provides non-single-chain antigen-binding units that is stabilized by leucine zipper sequences. The experimental design is particularly useful for generating and screening for Nsc Abus that remain the binding capabilities to their respective antigens within a cell. The present invention also provides recombinant polynucleotides, host cells and kits comprising the vectors. Further provided by the invention are methods of using the subject vectors.

15 Claims, 5 Drawing Sheets

OTHER PUBLICATIONS

Olsnes, et al., (1981) "Chimeric Toxins" *Pharmac. Ther.* 15:355-381.

Orlandi, et al., (1989) "Cloning Immunolglobulin Variable Domains for Expression by the Polymerase Chain Reaction" *Proc. Natl. Acad. Sci. USA* 86:3833-3837.

Sambrook, eds., (1989) "Molecular Cloning: A Laboratory Manual" 2nd Edition [Table of Contents Provided].

Sastry, et al., (1989) "Cloning of the Immunological Repertoire in *Escherichia coli* for Generation of Monoclonal Catalytic Antibodies: Construction of a Heavy Chain Variable Region-Specific cDNA Library" *Proc. Natl. Acad. Sci. USA* 86:5728-5732.

Shalaby, et al., (1992) "Development of Humanized Bispecific Antibodies Reactive with Cytotoxic Lymphocytes and Tumor Cells Overexpressing the HER2 Protooncogene" *J. Exp. Med.* 175:217-225.

Stemmer, et al. (1993) "Selection of an Active Single Chain Fv Antibody from a Protein Linker Library Prepared by Enzymatic Inverse PCR" *Biotechniques* 14(2):256-265.

Tempest, et al., (1991) "Reshaping a Human Monoclonal Antibody to Inhibit Human respiratory Syncytial Virus Infection *In Vivo* " *Biotechnology* 9:266-271.

Thorpe, et al., (1982) "Monoclonal Antibodies in Clinical Medicine" *Academic Press* 168-201.

Vidal, et al., (1995) "Identification of Essential Nucleotides in an Upstream Repressing Sequence of Sacchyaromyces Cerevisiae by Selection for Increased Expression of TRK2" *Proc. Natl. Acad. Sci USA* 92:2370-2374.

Vitetta, et al., (1987) "Redesigning Nature's Poisons to Create Anti-Tumor Reagents" *Science* 238:1098-1104.

Winter, et al., (1987) "Man-Made Antibodies" *Nature* 349:293-299.

\* cited by examiner

SEQ ID NO. 3
GAGCTCGGTACCTTGAAAGAT<u>GGCCCAGCCGGCC</u>ACTAGT<u>GCGGCCGC</u>ACTGGAGCGGATCGC
                      Sfi I                Not I
TCGGCTAGAGGAAAAAGTGAAAACCTTGAAAGCGCAAAACTCCGAGCTGGCATCCACGGCCAA
CATGCTCAGGGAACAGGTGGCACAGCTTAAGCAGAAAGTCATGAACCAGTATCCTTATGACGTG
CCTGACTATGCCGAGGACCTTAAGAAGAAGAGAAAGGTGGCGTGAGATCTGCAG

SEQ ID NO. 4

CTCGAGCTTGAAAGAT<u>GGCCCAGCCGGCC</u>ACCGGT<u>GCGGCCGC</u>ACTGAC
                   Sfi I                   Not I
AGATACACTCCAAGCGGAGACAGATCAACTTGAAGATGAGAAGTCTGCG
TTGCAGACTGAGATTGCCAATCTGCTGAAAGAGAAGGAAAAACTGGAGT
TTATTTTGGCAGCCCACTCGAG

SEQUENCE LISTING

<160> NUMBER OF SEQ ID NOS: 4

<210> SEQ ID NO 1
<211> LENGTH: 32
<212> TYPE: DNA
<213> ORGANISM: Artificial sequence
<220> FEATURE:
<223> OTHER INFORMATION: homologous to ras gene

<400> SEQUENCE: 1
atggccatgg tcacagaata caagcttgtg gt                        32

<210> SEQ ID NO 2
<211> LENGTH: 35
<212> TYPE: DNA
<213> ORGANISM: Artificial sequence
<220> FEATURE:
<223> OTHER INFORMATION: homologous to ras gene

<400> SEQUENCE: 2
taagaatgcg gccgctcagg acagcacaca tttgc                     35

<210> SEQ ID NO 3
<211> LENGTH: 244
<212> TYPE: DNA
<213> ORGANISM: Artificial sequence
<220> FEATURE:
<223> OTHER INFORMATION: vector sequence containing Sfi I and NotI
      restriction sites

<400> SEQUENCE: 3
gagctcggta ccttgaaaga tggcccagcc ggccactagt gcggccgcac tggagcggat      60
cgctcggcta gaggaaaaag tgaaaacctt gaaagcgcaa aactccgagc tggcatccac     120
ggccaacatg ctcagggaac aggtggcaca gcttaagcag aaagtcatga accagtatcc     180
ttatgacgtg cctgactatg ccgaggacct taagaagaag agaaaggtgg cgtgagatct     240
gcag                                                                  244

<210> SEQ ID NO 4
<211> LENGTH: 169
<212> TYPE: DNA
<213> ORGANISM: Artificial sequence
<220> FEATURE:
<223> OTHER INFORMATION: vector sequence containing Sfi I and NotI
      restriction sites

<400> SEQUENCE: 4

```
                                -continued ctcgagcttg aaagatggcc cagccggcca ccggtgcggc cgcactgaca gatacactcc       60
aagcggagac agatcaactt gaagatgaga agtctgcgtt gcagactgag attgccaatc      120
tgctgaaaga gaaggaaaaa ctggagttta ttttggcagc ccactcgag               169
```

COMPOSITIONS AND METHODS FOR GENERATING ANTIGEN-BINDING UNITS

CROSS-REFERENCE TO RELATED APPLICATIONS

This application claims the priority benefit of U.S. Provisional Patent Application 60/314,489, filed Aug. 22, 2001, pending, which is hereby incorporated herein by reference in its entirety.

TECHNICAL FIELD

This invention is in the field of immunology. Specifically, the invention relates to the generation of non-single-chain antigen-binding units that are stabilized by leucine zipper sequences. The experimental design is particularly useful for generating and screening for non-single-chain antigen-binding units that remain the binding capabilities to their respective antigens within a cell. The compositions and methods embodied in the present invention are particularly useful for identifying antigen-binding units that are of major diagnostic and/or therapeutic potential.

BACKGROUND OF THE INVENTION

The immune response of a vertebrate system provides a protective system that distinguishes foreign entities from entities native to the vertebrate system. Immune responses are the primary responsibilities of the B and T lymphocytes, which mediate the humoral response and the cell-mediated response, respectively. The humoral response is elicited by the B-cells which secrete antibodies (also known as immunoglobulins). Antibodies or immunoglobulins are molecules that recognize and bind to specific cognate antigens. Because of their exclusive specificities, antibodies, particularly monoclonal antibodies, are essential tools for analyzing the functions of biological molecules. Antibodies can be used to detect the protein expression levels, identify the protein-protein interaction complexes, localize the cellular compartment and tissue specificity, and analyze gene functions by neutralizing the gene product. Furthermore, antibodies have been widely used in the diagnosis and treatment of a variety of human diseases.

The basic immunoglobulin (Ig) in vertebrate systems is composed of two identical light ("L") chain polypeptides (approximately 23 kDa), and two identical heavy ("H") chain polypeptides (approximately 53 to 70 kDa). The four chains are joined by disulfide bonds in a "Y" configuration. At the base of the Y, the two H chains are bound by covalent disulfide linkages. The L and H chains are organized in a series of domains. The L chain has two domains, corresponding to the C region ("CL") and the other to the V region ("VL"). The H chain has four domains, one corresponding to the V region ("VH") and three domains (CH1, CH2 and CH3) in the C region. The antibody contains two arms (each arm being a Fab fragment), each of which has a VL and a VH region associated with each other. It is this pair of V regions (VL and VH) that differ, from one antibody to another (due to amino acid sequence variations), and which together are responsible for recognizing the antigen and providing an antigen-binding site. More specifically, each V region is made up from three complementarity determining regions (CDR) separated by four framework regions (FR). The CDR's are the most variable part of the variable regions, and they perform the critical antigen binding function. The CDR regions are derived from many potential germ line sequences via a complex process involving recombination, mutation and selection.

Research in recent years has demonstrated that the function of a binding antigen can be performed by fragments of a whole antibody. Exemplary antigen binding fragments are (i) the Fab fragment consisting of the VL, VH, CL and CH1 domains; (ii) the Fd fragment consisting of the VH and CH1 domains; (iii) the dAb fragment (Ward, E. S. et al., Nature 341, 544–546 (1989) which consists of a VH domain; (iv) isolated CDR regions; and (v) F(ab')$_2$ fragments, a bivalent fragment comprising two Fab fragments linked by a disulfide bridge at the hinge region; and (vi) the Fv fragment consisting of the VL and VH domains of a single arm of an antibody. The Fv fragment is the smallest functional unit required for high affinity binding of antigen.

One major challenge in the antibody field has been to reconstitute a vast diverse repertoire of immunoglobulins that mimics the immunoglobulin pool in the human immune system. Such a repertoire generally has a complexity ranging from $10^8$ to $10^{13}$ distinct immunoglobulins. The generation of such a repertoire would greatly facilitate the identification and production of immunoglobulins capable of interacting specifically with therapeutic targets. However, the design and production of such a repertoire has traditionally been hampered by the lack of a stabilizing means for assembly of the minimal functional unit, namely the Fv fragment. It is a well-known problem in the art that the VH and VL regions, when expressed alone, have very low interaction energy (Glockshuber et al. (1990) Biochemistry 29(6):1362–1367). The two components dissociate at low protein concentrations and are too unstable for many applications at physiological body temperature. It is also a long-recognized technical obstacle that large proteins, such as whole antibodies (albeit extremely stable), do not express at an appreciable level in the host cell, thus rendering the construction of a highly diverse antibody repertoire very difficult.

More recently, three approaches have been developed to generate stable VL and VH complexes. However, each of these techniques bears a number of intrinsic limitations; and none of them circumvents the aforementioned technical hurdles completely. The first approach uses a peptide linker to connect the VL and VH as a single-chain ("scFv") (Huston et al. (1988) Proc. Natl. Acad. Sci. U.S.A 85:5879–5883). While the resulting scFv exhibits substantial antigen-binding activity, not all antibodies can be made as single chains and still retain high binding affinity (Huston et al. (1988) Proc. Natl. Acad. Sci. U.S.A. 85:5879–5883; Stemmer et al. (1993) Biotechniques 14(2): 256–265). In part, this is due to the interference of linker sequences with the antigen binding sites. Furthermore, the propensity of single-chain antigen-binding units to aggregate inside a cell also hampers their intracellular antigen-binding capabilities. To efficiently isolate those single-chain antigen-binding units with the desired intracellular binding capabilities, a vast diverse repertoire of distinct single-chain antibody molecules that are amenable for an in vivo selection must be generated.

The second approach involves inserting a pair of cysteine residues in the VL and VH regions to generate a disulfide-bond stabilized Fv ("dsFv") (Brinkmann et al. (1993) Proc. Natl. Acad. Sci. U.S.A. 90(16): 7538–7542). The incorporated disulfide linkage, however, is unstable under reducing conditions in many host cells. For instance, in cytosol of E. Coli, the inter-molecular disulfide bond is often insufficient to stabilize the VL and VH complex. Moreover, this method typically requires 3-dimensional structural information of the V regions to ensure that the cysteine pair is inserted in a proper place without disruption the binding activity. Because the 3-dimensional information of a vast majority of the existing antibodies is unknown, this approach has little practical utility, and is particularly unsuited for antibody library construction, especially for constructing antibody repertoires derived from B cells. The third approach for stabilizing the VL and VH regions utilizes the disulfide bonds native to the CH1 and CL domains. This method proceeds with grafting a disulfide-bond linked CH1 and CL domains to the C-termini of the VL and VH regions in order to reconstitute a Fab fragment. While the resulting Fab fragment is generally more stable and often exhibits higher binding affinity than scFv, Fab is not optimal for high level expression and antibody repertoire construction due to its large size.

Certain dimerization sequences that form coiled-coil structures have also been employed to assemble multivalent antibodies. Specifically, U.S. Pat. No. 5,932,448 describes a bispecific $F(ab')_2$ heterodimer linked by the Fos and Jun leucine zippers. However, the binding sites are still stabilized by the constant regions (e.g. CH1) contained in the $F(ab')_2$ molecule.

Thus, there remains a considerable need for improved compositions and methods to generate stable antigen-binding units and repertoires thereof to effect identification of therapeutic antigen-binding units. An improved antigen-binding unit would be more stable than a Fv fragment, but would preferably be smaller than a Fab fragment to allow large-scale production and efficient display. Such antigen-binding unit would also serve as a building block for constructing multivalent and/or multispecific antibodies. The present invention satisfies these needs and provides related advantages as well.

SUMMARY OF THE INVENTION

A principal aspect of the present invention is the design of a non-single-chain antigen-binding unit that is stabilized by leucine zipper sequences. The experimental design is particularly useful for generating and screening for non-single-chain antigen-binding units that remain the binding capabilities to their respective antigens within a cell. Antigen-binding units capable of binding to their respective antigens (i.e. "intracellular" antigen-binding units) inside a cell are of tremendous research and therapeutic value. The ability of these binding units to specifically inhibit a protein's function and/or expression allows one to elucidate the biological function of the protein by creating, essentially, a protein-specific "knock-out" cell. Thus, the generation of these antibodies can greatly facilitates functional genomics studies.

Specifically, the present invention provides a non-single-chain antigen-binding unit comprising: a non-single-chain antigen-binding unit comprising: (a) a light (L) chain polypeptide comprising a light (L) chain variable region fused to a first leucine zipper sequence; (b)a heavy (H) chain polypeptide comprising a heavy (H) chain variable region fused to a second leucine zipper sequence; wherein the L chain and the H chain polypeptides dimerize to form an antigen-binding site through an interaction between the first and second leucine zipper sequences. In one aspect of this embodiment, the subject non-single-chain antigen-binding unit contains a first leucine zipper sequence which is Fos leucine zipper, and the second leucine zipper sequence which is Jun leucine zipper, or vise versa. In another aspect, either the L chain or the H chain polypeptide of the subject binding unit is further fused to a gene activation moiety region. In yet another aspect, the L or H chain polypeptide further comprises a flexon that is flanked by the L chain variable region and the first leucine zipper sequence. The L or H polypeptide may contain sequences derived from human or non-human antibodies.

The present invention also provides a recombinant polynucleotide comprising a coding sequence that encodes the L or H chain polypeptide of the subject antigen-binding unit. The embodied recombinant polynucleotide may comprise a coding sequence that encodes either an L or H chain polypeptide that is fused to a gene activation moiety region.

The present invention further provides a vector comprising the subject recombinant polynucleotide. The vector can be an expression vector or cloning vector. The invention also provides a kit comprising the subject vector in suitable packaging.

Also included in the invention is a selectable library of expression vector encoding a repertoire of antigen-binding units, comprising more than one invention vector. Further embodied in the invention are host cells expressing the recombinant polynucleotides or vectors.

The present invention includes a method of generating a non-single-chain antigen-binding unit in a yeast cell. The methods involves co-expressing (a) a light (L) chain polypeptide comprising a light (L) chain variable region fused to a first leucine zipper sequence; and (b) a heavy (H) chain polypeptide comprising a heavy (H) chain variable region fused to a second leucine zipper sequence, wherein the L and H chain polypeptides dimerize to form an antigen-binding site through an interaction between the first and second leucine zipper sequences.

In addition, the invention provides a method of identifying a non-single-chain antigen-binding unit that is immunoreactive with a desired antigen. The method comprises the steps of: (a) recombinantly co-expressing within a population of yeast cells (i) a reporter gene operably linked to a first DNA-binding-protein recognition site (DNA-BPRS); (ii) a first antigen fusion gene encoding the desired antigen fused in-frame with a first DNA-binding moiety which specifically binds to said first DNA-BPRS; (iii) a plurality of expression vectors that encodes a genetically diverse repertoire of antigen-binding units, each antigen-binding unit comprising a variable region of a first antibody chain fused to a first dimerization sequence, and a variable region of a second antibody chain fused to a second dimerization sequence and a gene activation moiety; wherein the variable regions of the first and second antibody chains dimerize to form an antigen-binding site through an interaction between the first and second dimerization sequences; and (b) detecting expression of said reporter gene, wherein an increase in the expression indicates a specific binding between an antigen binding fragment and the desired antigen, thereby identifying an antigen binding unit that is immunoreactive with the desired antigen. The step of co-expression of a plurality of expression vectors may comprise mating a first population of yeast cells that carries expression vectors encoding a repertoire comprising variable regions of a first antibody chain, with a second population of yeast cells that carries expression vectors encoding a repertoire comprising variable regions of a second antibody chain.

Where desired, the method further comprises the step of counter selecting yeast cells that express the reporter gene independent of the specific interaction between an antigen binding fragment and the desired antigen. Such a counterselection typically involves (a) recombinantly co-expressing within the population of yeast cells (i) counterselectable gene operably linked to a second DNA-binding protein recognition site (DNA-BPRS); (ii) a second antigen fusion gene encoding a second antigen fused in-frame with a second DNA-binding moiety which specifically binds to the second DNA-BPRS, wherein the second antigen differs structurally from the first antigen; (b) culturing the yeast cells under condition suitable for expression for the reporter gene and the counterselectable gene; and (c) detecting growth of yeast cells and expression of the reporter gene, wherein the growth of the yeast cells and an increase in the reporter gene expression indicate that a specific binding between an antigen-binding unit and the desired antigen has occurred.

In one aspect of the method embodiments, the reporter gene is selected from the group consisting of LEU2, TRP1, HIS3, LacZ, URA3, and MEL. The counterselectable gene is selected from the group consisting of URA3, LYS5, GAL1, CYH2, and CAN1. The counterselectable gene is integrated into the genome of the population of mating or mated yeast cells.

In another aspect, the DNA-binding-protein recognition site comprises at least one binding site for a protein selected from the group consisting of GAL4, LexA, and Ace1. In yet another aspect, the DNA-binding moiety comprises the DNA-binding domain of a protein selected from the group consisting of GAL4, LexA, and Ace1. In still yet another aspect, the gene activating moiety comprises the transcription activation domain of GAL4, or VP16.

EXPLAINATION OF ABBREVIATIONS USED HEREIN

1. Nsc: Non-single chain
2. Sc: Sing-chain
3. Abu: Antigen-binding unit
4. Abus: Antigen-binding units
4. L chain: Light chain
5. H chain: Heavy chain
6. VL: Light chain variable region
7. VH: Heavy chain variable region

MODE(S) FOR CARRYING OUT THE INVENTION

Figures 1A, 1B:
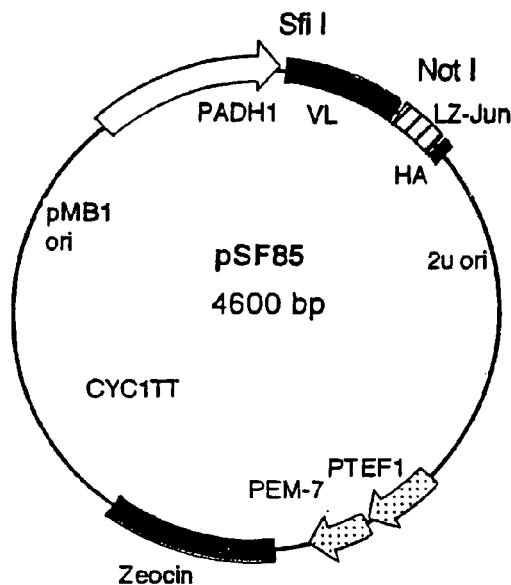
FIG. 1 is a schematic representation depicting the plasmid designated pSF85. pSF85 is a shuttle vector for expressing the light chain or VL segment fused with Jun leucine zipper domain and HA tag (A). It contains the cloning sites Sfi I and Not I for inserting the light chain or VL segment (e.g. VL of the anti-Ras antibody) and the sequences for encoding the Jun leucine zipper and HA tag (B).

Throughout this disclosure, various publications, patents and published patent specifications are referenced by an identifying citation. The disclosures of these publications, patents and published patent specifications are hereby incorporated by reference into the present disclosure.

General Techniques:

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Matthews, PLANT VIROLOGY, $3^{rd}$ edition (1991); Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

DEFINITIONS

The terms "polypeptide", "peptide" and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

A polypeptide or amino acid sequence "derived from" a designated protein refers to the origin of the polypeptide. Preferably, the polypeptide have an amino acid sequence that is essentially identical to that of a polypeptide encoded in the sequence, or a portion thereof wherein the portion consists of at least 10–20 amino acids, preferably at least 20–30 amino acids, more preferably at least 30–50 amino acids, or which is immunologically identifiable with a polypeptide encoded in the sequence. This terminology also includes a polypeptide expressed from a designated nucleic acid sequence.

A "chimeric" or "hybrid" protein contains at least one fusion polypeptide comprising regions in a different position in the sequence than that occurs in nature. The regions may normally exist in separate proteins and are brought together in the fusion polypeptide; or they may normally exist in the same protein but are placed in a new arrangement in the fusion polypeptide. A chimeric or hybrid protein may be created, for example, by chemical synthesis, or by creating and translating a polynucleotide in which the peptide regions are encoded in the desired relationship.

A "multimeric protein" as used herein refers to a globular protein containing more than one separate polypeptide or protein chain associated with each other to form a single globular protein in vitro or in vivo. The multimeric protein may consist of more than one polypeptide of the same kind to form a "homomultimer." Alternatively, the multimeric protein may also be composed of more than one polypeptide of distinct sequences to form a "heteromultimer." Thus, a "heteromultimer" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where more than two polypeptides are present. Exemplary structures for the heteromultimer include heterodimers (e.g. Fab fragments, diabodies, Fv fragments dimerized via the interaction of a first and second leucine zipper,) trimeric G-proteins, heterotetramers (e.g. F(ab')$_2$ fragments) and further oligomeric structures.

A "first dimerization sequence" refers to any sequence which is capable, or is or was associated with a "second dimerization sequence" to form a dimeric structure, wherein the second heterodimerization sequence differs in amino acid sequence by at least one amino acid residue.

The term "antibody" as used herein refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units" ("Abus"). Abus can be broadly divided into "single-chain" ("Sc") and "non-single-chain" ("Nsc") types based on their molecular structures. The terms "the fist" or "the second" antibody chain as applied to an antigen-binding unit refers the light or the heavy antibody chain.

Also encompassed within the terms "antibodies" and "Abus" are immunoglobulin molecules of a variety of species origins including invertebrates and vertebrates. The term "human" as applies to an antibody or an Abu refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fe), typically that of a human immunoglobulin.

As used herein, a "non-single-chain antigen-binding unit" ("Nsc Abu") refers to a heteromultimer comprising a light-chain polypeptide and a heavy-chain polypeptide. By "light-chain polypeptide" is meant that the polypeptide contains sequences sharing derived from a light chain of an immunoglobulin. Likewise, "heavy-chain polypeptide" is meant that the polypeptide contains sequences sharing derived from a heavy chain of an immunoglobulin. Preferred examples of the Nsc Abus include (i) an Fv fragment stabilized by the leucine zipper sequences disclosed herein; (ii) any other monovalent and multivalent molecules comprising at least one Fv fragment stabilized by the leucine zipper sequences disclosed herein; (iii) an Fab fragment consisting of the VL, VH, CL and CH1 domains, in which the antigen-binding variable regions are stabilized via an interaction between the leucine zippers; (iv) an F(ab')2 fragment, a bivalent fragment comprising two Fab fragments linked by a disulfide bridge at the hinge region, each Fab fragment being stabilized through an interaction between the two leucine zippers.

As noted above, a Nsc Abus can be either "monovalent" or "multivalent." Whereas the former has one binding site per antigen-binding unit, the latter contains multiple binding sites capable of binding to more than one antigen of the same or different kind. Depending on the number of binding sites, a Nsc Abus may be bivalent (having two antigen-binding sites), trivalent (having three antigen-binding sites), tetravalent (having four antigen-binding sites), and so on.

Multivalent Nsc Abus can be further classified on the basis of their binding specificities. A "monospecific" Nsc Abu is a molecule capable of binding to one or more antigens of the same kind. A "multispecific" Nsc Abu is a molecule having binding specificities for at least two different antigens. While such molecules normally will only bind two distinct antigens (i.e. bispecific Abus), antibodies with additional specificities such as trispecific antibodies are encompassed by this expression when used herein. Examples of bispecific antigen binding units include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; bispecific Abus with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); bispecific Abus which can be used as fibrinolytic agents such as anti-fibrin/anti-tissue plasminogen activator (tPA), anti-fibrin/anti-urokinase-type plasminogen activator (uPA); bispecific antigen-binding units for targeting immune complexes to cell surface receptors such as anti-low density lipoprotein (LDL)/anti-Fc receptor (e.g. Fcγ RI, FcγRII or FcγRIII); bispecific Abus for use in therapy of infectious diseases such as anti-CD3/anti-herpes simplex virus (HSV), anti-T-cell receptor:CD3 complex/anti-influenza, anti-FcγR/anti-HIV; bispecific Abus for tumor detection in vitro or in vivo such as anti-CEA/anti-EOTUBE, anti-CEA/anti-DPTA, anti-p185$^{HER2}$/anti-hapten; BsAbs as vaccine adjuvants (see Fanger et al., supra); and bispecific Abus as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-.beta.-galactosidase (see Nolan et al., supra). Examples of trispecific antibodies include anti-CD3/anti-CD4/anti-CD37, anti-CD3/anti-CD5/anti-CD37 and anti-CD3/anti-CD8/anti-CD37.

As used herein, a "single-chain antigen-binding unit" ("Sc Abu") refers to a monomeric Abu. Although the two domains of the Fv fragment are coded for by separate genes, a synthetic linker can be made that enables them to be made as a single protein chain (i.e. single chain Fv ("scFv") as described in Bird et al. (1988) *Science* 242:423–426 and Huston et al. (1988) *PNAS* 85:5879–5883) by recombinant methods. A preferred single-chain antigen-binding unit contains VL and VH regions that are linked together and stabilized by a site-specific recombination sequence including but not limited to loxP site. The scFvs can be assembled in any order, for example, VH—(first heterodimerization sequence)-(second heterodimerization sequence)—VL, or $V_L$—first heterodimerization sequence)-(second heterodimerization sequence)—VH.

A "repertoire of antigen-binding units" refers to a plurality of antigen-binding units, at least two of which exhibit distinct binding specificities. A genetically diverse repertoire of antigen-binding units refers to a plurality of antigen-binding units, the majority and if not all of the antigen-binding units exhibit unique binding specificities with respect to each other. Genetically diverse repertoire typically has a complexity of at least $10^6$ to $10^{13}$, preferably between $10^7$ to $10^9$, more preferably between $10^8$ to $10^{10}$, even more preferably between $10^8$ to $10^{11}$ distinct antigen-binding units.

An antibody or Abu "specifically binds to" or "immunoreactive with" an antigen if it binds with greater affinity or avidity than it binds to other reference antigens including polypeptides or other substances.

The terms "intracellular binding capability" and "binds intracellularly" refers to the ability of an antigen-binding units to bind their respective antigens within a cell.

"Antigen" as used herein means a substance that is recognized and bound specifically by an antibody. Antigens can include peptides, proteins, glycoproteins, polysaccharides and lipids; portions thereof and combinations thereof.

For the class of proteinaceous antigens, the antigens may be membrane, cytosolic, nuclear or secreted peptides or proteins.

As used herein, the term "surface antigens" refers to the plasma membrane components of a cell. It encompasses integral and peripheral membrane proteins, glycoproteins, polysaccharides and lipids that constitute the plasma membrane. An "integral membrane protein" is a transmembrane protein that extends across the lipid bilayer of the plasma membrane of a cell. A typical integral membrane protein consists of at least one "membrane spanning segment" that generally comprises hydrophobic amino acid residues. Peripheral membrane proteins do not extend into the hydrophobic interior of the lipid bilayer and they are bound to the membrane surface by noncovalent interaction with other membrane proteins.

The terms "membrane", "cytosolic", "nuclear" and "secreted" as applied to cellular proteins specify the extracellular and/or subcellular location in which the cellular protein is mostly, predominantly, or preferentially localized.

"Cell surface receptors" represent a subset of membrane proteins, capable of binding to their respective ligands. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions.

"Domain" refers to a portion of a protein that is physically or functionally distinguished from other portions of the protein or peptide. Physically-defined domains include those amino acid sequences that are exceptionally hydrophobic or hydrophilic, such as those sequences that are membrane-associated or cytoplasm-associated. Domains may also be defined by internal homologies that arise, for example, from gene duplication. Functionally-defined domains have a distinct biological function(s). The ligand-binding domain of a receptor, for example, is that domain that binds ligand. An antigen-binding domain refers to the part of an antigen-binding unit or an antibody that binds to the antigen. Functionally-defined domains need not be encoded by contiguous amino acid sequences. Functionally-defined domains may contain one or more physically-defined domain. Receptors, for example, are generally divided into the extracellular ligand-binding domain, a transmembrane domain, and an intracellular effector domain.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

A "cell line" or "cell culture" denotes bacterial, plant, insect or higher eukaryotic cells grown or maintained in vitro. The descendants of a cell may not be completely identical (either morphologically, genotypically, or phenotypically) to the parent cell.

A "defined medium" refers to a medium comprising nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: a)

all essential amino acids, and usually the basic set of twenty amino acids plus cysteine; b) an energy source, usually in the form of a carbohydrate such as glucose; c) vitamins and/or other organic compounds required at low concentrations; d) free fatty acids; and e) trace elements, where trace elements are defined as inorganic compounds or naturally occurring elements that are typically required at very low concentrations, usually in the micromolar range. The defined medium may also optionally be supplemented with one or more components from any of the following categories: a) one or more mitogenic agents; b) salts and buffers as, for example, calcium, magnesium, and phosphate; c) nucleosides and bases such as, for example, adenosine and thymidine, hypoxanthine; and d) protein and tissue hydrolysates.

As used herein, the term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart.

Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

"Linked" and "fused" or "fusion" are used interchangeably herein. These terms refer to the joining together of two more chemical elements or components, by whatever means including chemical conjugation or recombinant means. An "in-frame fusion" refers to the joining of two or more open reading frames (OFRs) to form a continuous longer OFR, in a manner that maintains the correct reading frame of the original OFRs. Thus, the resulting recombinant fusion protein is a single protein containing two ore more segments that correspond to polypeptides encoded by the original OFRs (which segments are not normally so joined in nature.) Although the reading frame is thus made continuous throughout the fused segments, the segments may be physically or spatially separated by, for example, in-frame linker sequence (e.g. "flexon"), as described infra.

In the context of polypeptides, a "linear sequence" or a "sequence" is an order of amino acids in a polypeptide in an amino to carboxyl terminus direction in which residues that neighbor each other in the sequence are contiguous in the primary structure of the polypeptide. A "partial sequence" is a linear sequence of part of a polypeptide which is known to comprise additional residues in one or both directions.

"Heterologous" means derived from a genotypically distinct entity from the rest of the entity to which it is being compared. For example, a promoter removed from its native coding sequence and operatively linked to a coding sequence other than the native sequence is a heterologous promoter. The term "heterologous" as applied to a polynucleotide, a polypeptide, means that the polynucleotide or polypeptide is derived from a genotypically distinct entity from that of the rest of the entity to which it is being compared. For instance, a heterologous polynucleotide or antigen may be derived from a different species origin, different cell type, and the same type of cell of distinct individuals.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Recombinant" as applied to a polynucleotide means that the polynucleotide is the product of various combinations of cloning, restriction and/or ligation steps, and other procedures that result in a construct that is distinct from a polynucleotide found in nature.

The terms "gene" or "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof.

"Operably linked" or "operatively linked" refers to a juxtaposition wherein the components so described are in a relationship permitting them to function in their intended manner. For instance, a promoter sequence is operably linked to a coding sequence if the promoter sequence promotes transcription of the coding sequence.

A "fusion gene" is a gene composed of at least two heterologous polynucleotides that are linked together.

A gene "database" denotes a set of stored data which represent a collection of sequences including nucleotide and peptide sequences, which in turn represent a collection of biological reference materials.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectively referred to as gene product. If the polynucleotide is derived from genomic DNA, expression may include splicing of the mRNA in a eukaryotic cell.

A "subject" as used herein refers to a biological entity containing expressed genetic materials. The biological entity is preferably plant, animal, or microorganisms including bacteria, viruses, fungi, and protozoa. Tissues, cells and their progeny of a biological entity obtained in vivo or cultured in vitro are also encompassed.

A "vector" is a nucleic acid molecule, preferably self-replicating, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions.

An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

A "replicon" refers to a polynucleotide comprising an origin of replication (generally referred to as an ori sequence) which allows for replication of the polynucleotide in an appropriate host cell. Examples of replicons include episomes (such as plasmids), as well as chromosomes (such as the nuclear or mitochondrial chromosomes).

Antigen-Binding Units (Abus) of the Present Invention

A central aspect of the present invention is the design of a non-single-chain antigen-binding unit that is stabilized by leucine zipper sequences. The experimental design is particularly useful for generating and screening for Nsc Abus that remain the binding capabilities to their respective antigens within a cell. Distinguished from the previously reported bispecific Fab Abus (U.S. Pat. Nos. 5,932,448 and 5,582,996) whose antigen-binding sites are stabilized by the constant regions (e.g. CH1), the antigen-binding sites of the subject Abus are reconstituted via the interaction between a first and second leucine zipper sequences. The subject Nsc Abus may be further distinguished from the previously employed sequences at the structural level as detailed below.

In one embodiment, the present invention provides a non-single-chain antigen-binding unit comprising: (a) a light (L) chain polypeptide comprising a light (L) chain variable region fused to a first leucine zipper sequence; (b) a heavy (H) chain polypeptide comprising a heavy (H) chain variable region fused to a second leucine zipper sequence; wherein the L chain and the H chain polypeptides dimerize to form an antigen-binding site through an interaction between the first and second leucine zipper sequences. In one aspect, the first leucine zipper sequence is Fos leucine zipper and the second lecuine zipper sequence is Jun leucine zipper, or vise versa. In another aspect, either the L chain or the H chain polypeptide is further fused to a gene activation moiety region.

Selection of Leucine Zipper Sequences:

The leucine zipper have been defined in the art as a stretch of about 35 amino acids containing 4–5 leucine residues separated from each other by six amino acids (Maniatis and Abel, (1989) Nature 341:24). The leucine zipper has been found to occur in a variety of eukaryotic DNA-binding proteins, such as GCN4, C/EBP, c-fos gene product (Fos), c-jun gene product (Jun), and c-myc gene product. In these proteins, the leucine zipper creates a dimerization interface wherein proteins containing leucine zippers may form stable homodimers and/or heterodimers. Molecular analysis of the protein products encoded by two proto-oncogenes, c-fos and c-jun, has revealed such a case of preferential heterodimer formation (Gentz et al., (1989) *Science* 243:1695; Nakabeppu et al., (1988) *Cell* 55:907; Cohen et al., (1989) *Genes Dev.* 3:173). Synthetic peptides comprising the leucine zipper regions of Fos and Jun have also been shown to mediate heterodimer formation, and, where the amino-termini of the synthetic peptides each include a cysteine residue to permit intermolecular disulfide bonding, heterodimer formation occurs to the substantial exclusion of homodimerization.

Leucine zippers useful for constructing the subject Abus must form a stable complex. By "stable" is meant that the complex or dimer is sufficiently long-lasting to persist between the formation of the complex or dimer, and its subsequent detection and/or purification. The complex or dimer must be able to withstand whatever conditions exist or are introduced between the moment of formation and the moment of detection, these conditions being a function of the assay or reaction which is being performed. Preferably, the formation of the complex or dimer is carried out under physiological buffer conditions and at physiological body temperatures ranging from approximately room temperature to approximately 37° C. Intervening conditions which may optionally be present and which may dislodge a complex or dimer include washing, heating, adding additional solutes or solvents to the reaction mixture (such as denaturants), and competing with additional reacting species. Stable complex or dimer may be irreversible or reversible, but must meet the other requirements of this definition. Thus, a transient complex or dimer may form in a reaction mixture, but it does not constitute a stable complex if it dissociates spontaneously under physiological buffer conditions or as a result of a newly imposed condition or manipulation introduced before detection.

The leucine zippers of the present invention have the general structural formula known as the heptad repeat (Leucine-$X_1$-$X_2$-$X_3$-$X_4$-$X_5$-$X_6$)$_n$, where X may be any of the conventional 20 amino acids, but are most likely to be amino acids with alpha-helix forming potential, for example, alanine, valine, aspartic acid, glutamic acid, and lysine, and n may be 2 or greater, although typically n is 3 to 10, preferably 4 to 8, more preferably 4 to 5. Preferred sequences are the Fos or Jun leucine zippers.

Accordingly, the present invention encompasses the leucine zippers derived from Fos and Jun. In one aspect, the subject Jun zipper sequence is encoded by at least 45 nucleotide bases, preferably at least 85 nucleotide bases, and even more preferably by at least 100 nucleotide bases, each of which is essentially identical to a linear sequence of comparable length depicted in FIG. 1. In another aspect, the subject Fos zipper sequence is encoded by at least 45 nucleotide bases, preferably at least 85 nucleotide bases, and even more preferably by at least 100 nucleotide bases, each of which is essentially identical to a linear sequence of comparable length depicted in FIG. 2.

A linear sequence of peptide is "essentially identical" to another linear sequence, if both sequences exhibit substantial nucleotide or amino acid sequence homology. Generally, essentially identical sequences are at least about 60% identical with each other, after alignment of the homologous regions. Preferably, the sequences are at least about 70% identical; more preferably, they are at least about 80% identical; more preferably, they are at least about 90% identical; more preferably, the sequences are at least about 95% identical; still more preferably, the sequences are 100% identical.

In determining whether polypeptide sequences are essentially identical, a sequence that preserves the functionality of the polypeptide with which it is being compared is particularly preferred. Functionality may be established by different criteria, such as ability to form a heterodimer with a pairing leucine zipper.

The invention includes modified Fos and Jun leucine zippers which are functionally equivalent to the sequences exemplified herein. Modified polypeptides providing improved stability to the resulting Abus are preferred. Examples of modified polypeptides include those with conservative substitutions of amino acid residues, and one or more deletions or additions of amino acids which do not significantly deleteriously alter the heterodimerization specificity. Substitutions can range from changing or modifying one or more amino acid residues to complete redesign of a region as long as the pairwise affinity is maintained. Amino acid substitutions, if present, are preferably conservative substitutions that do not deleteriously affect folding or functional properties of the peptide. Groups of functionally related amino acids within which conservative substitutions can be made are glycine/alanine; valine/isoleucine/leucine; asparagine/glutamine; aspartic acid/glutamic acid; serine/threonine/methionine; lysine/arginine; and phenylalanine/tryosine/tryptophan. Polypeptides of this invention can be in glycosylated or unglycosylated form, can be modified post-translationally (e.g., acetylation, and phosphorylation) or can be modified synthetically (e.g., the attachment of a labeling group).

The leucine zippers should be linked to the VL or VH region in such a away that it will minimize any structural interference between the zipper sequences and the antigen-binding site of the resulting Abu. A variety of techniques is available in the art for designing a chimeric Abu with minimal internal structural interference. For instance, one approach involves the use of minimal zipper sequences containing only amino acid residues that are required for heterodimerization. The second approach is to link the zipper sequences to either N-terminus or C-terminus of the resulting Abu. The choice of either terminus will depend on the location of the biological active domain of the heteromultimer. For constructing a chimeric Abu whose antigen-binding site resides in the N-terminal half of the light and heavy chain variable regions, it is preferable to link the heterodimerization sequences to the C-terminus of a light or heavy chain. Another alternative design employs a "flexon" incorporated between the antigen-binding site and the heterodimerization sequence of the heteromultimer. "Flexon" as used herein, refers to a flexible polypeptide linker (or a nucleic acid sequence encoding such a polypeptide) which typically comprises amino acids having small side chains (e.g. glycine, alanine, valine, leucine, isoleucine, and serine). Incorporating flexons between one or more sites of the subject Abu may promote functionality by allowing them to assume a conformations relatively independent of each other. Such a construction generally provides additional flexibility to the antigen-binding domain. Suitable flexons preferably comprise between about four and about one hundred amino acids, more preferably about four to fifty amino acids, and even more preferably about four to fifteen amino acids.

Linking Gene Activation Moiety to Antigen-Binding Units (Abus):

In certain preferred embodiment, the Abu is expressed as a fusion with a gene activation moiety. The gene activation moiety facilitates the detection of specific binding of the Abu to an antigen in a eukaryotic cell. Such a specific binding is preferably detected in a yeast cell employing a two hybrid system.

The yeast two-hybrid system and its derivative systems have widely been used to detect protein-protein interactions (see, e.g. U.S. Pat. Nos. 5,283,173, 5,965,368, 5,948,620, 6,171,795, 6,132,963, 5,695,941, 6,187,535, 6,159,705, 6,057,101, 6,083,693, 5,928,868, 6,200,759, WO 95/14319, WO 95/26400). These well-established systems generally involve in vivo reconstitution of two separable domains of a transcription factor. The DNA-binding domain (DB) of the transcription factor is required for recognition of a chosen promoter. The transcription activation domain (AD) is required for contacting other components of the cell's transcriptional machinery. In these systems, the transcription factor is reconstituted through the use of hybrid proteins. One hybrid is composed of the AD and a first protein of interest. The second hybrid is composed of the DB and a second protein of interest. In detecting specific binding of an Abu to a desired antigen, the Abu is typically fused with the AD and the antigen is fused to the DB domain. Alternatively, the Abu is fused with the DB, and the antigen is fused to the AD. In case where the Abu binds to the antigen of interest, the AD and DB are brought into close physical proximity, thereby reconstituting the transcription factor. Specific binding of an Abu to a desired antigen can be measured by assaying the ability of the reconstituted transcription factor to activate transcription of a reporter gene.

By "DNA-binding domain" or "DB" is meant a polypeptide sequence which is capable of directing specific polypeptide binding to a particular DNA sequence (i.e., to a DNA-binding-protein recognition site or "DNA-BPRS). The term "domain" in this context is not intended to be limited to a discrete folding domain. Rather, consideration of a polypeptide as a DB for use in the fusion protein can be made simply by the observation that the polypeptide has a specific DNA-binding activity. Non-limiting examples of DB containing proteins are GAL4, LEX, and ACE1. As is apparent to one of ordinary skill in the art, the DNA binding domain need not be derived from proteins in a prokaryotic cell. Proteins of eukaryotic origin and exhibiting desired DNA binding activity can be used. For example, the DB portion of the fusion protein can include polypeptide sequences from eukaryotic DNA binding proteins as p53, Jun, Fos, GCN4, or GAL4. Likewise, the DNA binding portion of the fusion protein can be generated from viral proteins, such as the pappillomavirus E2 protein. Alternatively, the DNA binding domain can be generated by combinatorial mutagenic techniques, and represent a DB not naturally occurring in any organism. A variety of techniques have been described in the art for generating novel DNA binding proteins which can selectively bind to a specific DNA sequence (see, e.g. U.S. Pat. No. 5,198,346).

Where desired, the DNA binding domain can include oligomerization motifs. It is well known in the art that certain transcriptional regulators dimerize, with dimerization promoting cooperative binding of the two monomers to their cognate recognition elements. For example, where the fusion protein includes a LexA DNA binding domain, it can further include a LexA dimerization domain; this optional domain facilitates efficient LexA dimer formation. Because LexA binds its DNA binding site as a dimer, inclusion of this domain in the bait protein also optimizes the efficiency of operator occupancy (Golemis and Brent, (1992) *Mol. Cell Biol.* 12:3006). Other oligomerization motifs useful in the present invention will be readily recognized by those skilled in the art. Exemplary motifs include the tetramerization domain of p53 and the tetramerization domain of BCR-ABL. In addition, a variety of techniques are known in the art for identifying other naturally occurring oligomerization domains, as well as oligomerization domains derived from mutant or otherwise artificial sequences. See, for example, Zeng et al. (1997) *Gene* 185:245.

The term "gene activation moiety" refers to a stretch of amino acids which is capable of inducing the expression of a gene whose control region (i.e. the promoter) it is bound. A variety of gene activation moieties containing transcription activation domains are available in the art for constructing the subject vectors. Generally, the transcription activation domain of any transcription factor can be used. A preferred example is VP16. All of the essential elements of a two hybrid system, which include the DNA-binding-protein recognition site, the transcription activation, and the DNA-binding domain, may correspond to one transcription factor, or they can correspond to different transcription factors. Suitable DNA-binding-protein recognition sites include those for the yeast protein GAL4, the bacterial protein LexA, the yeast metal-binding factor Ace1. These binding sites can readily be used with a repressed promoter (e.g., a SPO13 promoter can be used as the basis for SPAL, SPEX and SPACE promoters, respectively, for a SPO13 promoter combined with GAL, LEX, and ACE1 DNA binding sites). Other useful transcription factors include the GCN4 protein of *S. cerevisiae* (see, e.g., Hope and Struhol, 1986, *Cell* 46:885–894) and the ADR1 protein of *S. cerevisiae* (see, e.g., Kumar et al., 1987, *Cell* 51:941–951).

By "reporter gene" is meant a gene whose expression can be assayed as a measure of the ability of an Abu to bind to an antigen of particular interest. The reporter genes may encode any protein that provides a phenotypic marker, for example: a protein that is necessary for cell growth or a toxic protein leading to cell death, e.g., a protein which confers antibiotic resistance or complements an auxotrophic phenotype; a protein detectable by a colorimetric/fluorometric assay leading to the presence or absence of color/fluorescence; or a protein providing a surface antigen for which specific antibodies/ligands are available. Non-limiting examples of reporter genes are lacZ, amino acid biosynthetic genes (e.g., the yeast LEU2, HIS3, LYS2, or TRP1), URA3 genes, nucleic acid biosynthetic genes, the bacterial chloramphenicol transacetylase (cat) gene, MEL, and the bacterial gus gene. Also included are those genes which encode fluorescent markers, such as the Green Fluorescent Protein gene.

The reporter genes may be further classified as "selectable," "counterselectable," or "selectable/counterselectable" reporter genes. By "selectable" reporter gene is meant a reporter gene which, when it is expressed under a certain set of conditions, confers a growth advantage on cells containing it. By "counterselectable" reporter gene is meant a reporter gene which, when it is expressed under a certain set of conditions, inhibits the growth of a cell containing it. Examples of counterselectable reporter genes include well-established marker sequences such as URA3, LYS2, LYS5, GAL1, CYH2, and CAN1. The term "selectable/counterselectable" as applied to a reporter gene refers to the reporter that is lethal to a cell when it is expressed under a certain set of conditions, but confers a selective growth advantage on cells when it is expressed under a different set of conditions. Thus, a single gene can be used as both a selectable reporter gene and a counterselectable reporter gene. Examples of selectable/counterselectable reporter genes include URA3, LYS2, and GAL1. In each aspect of the invention where a selectable/counterselectable reporter gene is employed, a combination of a selectable reporter gene and a counterselectable reporter gene can be used in lieu of a single selectable/counterselectable reporter gene. The reporter genes can be located on a plasmid or can be integrated into the genome of a haploid or diploid cell. Generally, the reporter genes are operably fused to a promoter that is specifically recognized by the DB. The reporter gene whose expression is to be assayed is operably fused to a promoter which has sequences that direct transcription of the reporter gene. The reporter gene is positioned such that it is expressed when a gene activating moiety of a transcription factor is brought into close proximity to the gene (e.g., by using hybrid proteins to reconstitute a transcription factor, or by covalently bonding the gene-activating moiety to a DNA-binding protein). The reporter gene can also be operably fused to regulatory sequences which render it highly responsive to the presence or absence of a transcription factor. For example, in the absence of a specific transcription factor, a highly responsive URA3 allele confers a $Ura^-$ $Foa^r$ phenotype on the cell. In the presence of a specific transcription factor, a highly responsive URA3 allele confers a $Ura^+$ $Foa^s$ phenotype on the cell. Where the cell carrying the reporter gene (i.e., a transformed yeast cell) normally contains a wild-type copy of the gene (e.g., the URA3 gene), the exogenous reporter gene can be integrated into the genome and replace the wild-type gene. Conventional methods and criteria can be used to connect a reporter gene to a promoter and to introduce the reporter gene into a cell.

Configurations and Modifications of Antigen-Binding Units (Abus):

The Abus of the present invention can adopt a variety of configurations. The smallest non-single chain Abu is a monovalent Fv fragment stabilized by the leucine zippers. This fragment is a dimeric protein composed of VL and VH regions, which dimerize via the interaction of the first and second heterodimerization sequences fused in-frame with the VL and VH regions, respectively. Where desired, the fragment may contain a short flexon sequence that provides additional flexibility to the VL and VH regions.

A more complex Nsc Abu is a multivalent molecule capable of binding to more than one antigen of the same kind (i.e. multivalent but monospecific) or different kind (i.e. multivalent and multispecific Abus). Typically, a multivalent Abu is a heteromultimer composed of more than one L and H chain polypeptides, in which either the L or H polypeptide or both contain more than one V region. Regardless of the configurations of the resulting Abu, its antigen-binding sites are stabilized via the interaction of the linked leucine zippers.

The Abus of this invention may contain sequences derived from human or non-human antibodies. Methods for humanizing non-human antibodies are well known in the art. "Humanized" antibodies are antibodies in which at least part of the sequence has been altered from its initial form to render it more like human immunoglobulins. In one version, the CDR regions comprise non human antibody sequences, while the V framework regions have also been converted human sequences. See, for example, EP 0329400. In another version, V regions are humanized by designing consensus sequences of human and mouse V regions, and converting residues outside the CDRs that are different between the consensus sequences.

In making humanized antibodies, the choice of framework residues can be critical in retaining high binding affinity. In principle, a framework sequence from any human antibodies can serve as the template for CDR grafting; however, it has been demonstrated that straight CDR replacement into such a framework can lead to significant loss of binding affinity to the antigen. Glaser et al. (1992) *J. Immunol.* 149:2606; Tempest et al. (1992) *Biotechnology* 9:266; and Shalaby et al. (1992) *J. Exp. Med.* 17:217. The more homologous a human antibody is to the original murine antibody, the less likely that the human framework will introduce distortions into the murine CDRs that could reduce affinity. Based on a sequence homology search against an antibody sequence database, the HuAb IC4 provides good framework homology to muM4TS.22, although other highly homologous HuAbs would be suitable as well, especially kappa L chains from human subgroup I or H chains from human subgroup III. Kabat et al. (1987). Various computer programs such as ENCAD (Levitt et al. (1983) *J. Mol. Biol.* 168:595) are available to predict the ideal sequence for the V region. The invention thus encompasses human antibodies with different V regions. It is within the skill of one in the art to determine suitable V region sequences and to optimize these sequences. Methods for obtaining antibodies with reduced immunogenicity are also described in U.S. Pat. No. 5,270,202 and EP 699,755.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved.

The invention also encompasses Abus conjugated to a chemically functional moiety. Typically, the moiety is a label capable of producing a detectable signal. These conjugated Abus are useful, for example, in detection systems such as quantitation of tumor burden, and imaging of metastatic foci and tumor imaging. Such labels are known in the art and include, but are not limited to, radioisotopes, enzymes, fluorescent compounds, chemiluminescent compounds, bioluminescent compounds substrate cofactors and inhibitors. See, for examples of patents teaching the use of such labels, U.S. Pat. Nos. 3,817,837; 3,850,752; 3,939,350; 3,996,345; 4,277,437; 4,275,149; and 4,366,241. The moieties can be covalently linked to Abus, recombinantly linked, or conjugated to Abus through a secondary reagent, such as a second antibody, protein A, or a biotin-avidin complex.

Other functional moieties include signal peptides, agents that enhance immunologic reactivity, agents that facilitate coupling to a solid support, vaccine carriers, bioresponse modifiers, paramagnetic labels and drugs. Signal peptides is a short amino acid sequence that directs a newly synthesized protein through a cellular membrane, usually the endoplasmic reticulum in eukaryotic cells, and either the inner membrane or both inner and outer membranes of bacteria. Signal peptides are typically at the N-terminal portion of a polypeptide and are typically removed enzymatically between biosynthesis and secretion of the polypeptide from the cell. Such a peptide can be incorporated into the subject Abus to allow secretion of the synthesized molecules.

Agents that enhance immunologic reactivity include, but are not limited to, bacterial superantigens. Agents that facilitate coupling to a solid support include, but are not limited to, biotin or avidin. Immunogen carriers include, but are not limited to, any physiologically acceptable buffers. Bioresponse modifiers include cytokines, particularly tumor necrosis factor (TNF), interleukin-2, interleukin-4, granulocyte macrophage colony stimulating factor and γ-interferons.

Suitable drug moieties include antineoplastic agents. Non-limiting examples are radioisotopes, vinca alkaloids such as the vinblastine, vincristine and vindesine sulfates, adriamycin, bleomycin sulfate, carboplatin, cisplatin, cyclophosphamide, cytarabine, dacarbazine, dactinomycin, duanorubicin hydrochloride, doxorubicin hydrochloride, etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, taxol, thioguanine, and uracil mustard.

Immunotoxins, including single chain molecules, can be produced by recombinant means. Production of various immunotoxins is well-known in the art, and methods can be found, for example, in "Monoclonal Antibody-toxin Conjugates: Aiming the Magic Bullet," Thorpe et al. (1982) *Monoclonal Antibodies in Clinical Medicine*, Academic Press, pp. 168–190; Vitatta (1987) *Science* 238:1098–1104; and Winter and Milstein (1991) *Nature* 349:293–299. Suitable toxins include, but are not limited to, ricin, radionuclides, pokeweed antiviral protein, Pseudomonas exotoxin A, diphtheria toxin, ricin A chain, fungal toxins such as restrictocin and phospholipase enzymes. See, generally, "Chimeric Toxins," Olsnes and Pihl, *Pharmac. Ther.* 15:355–381 (1981); and "Monoclonal Antibodies for Cancer Detection and Therapy," eds. Baldwin and Byers, pp. 159–179, 224–266, Academic Press (1985).

The chemically functional moieties can be made recombinantly for instance by creating a fusion gene encoding the Abu and the functional moiety. Alternatively, the Abu can be chemically bonded to the moiety by any of a variety of well-established chemical procedures. For example, when the moiety is a protein, the linkage may be by way of heterobifunctional cross linkers, e.g., SPDP, carbodiimide glutaraldehyde, or the like. The moieties may be covalently linked, or conjugated, through a secondary reagent, such as a second antibody, protein A, or a biotin-avidin complex. Paramagnetic moieties and the conjugation thereof to antibodies are well-known in the art. See, e.g., Miltenyi et al. (1990) *Cytometry* 11:231–238.

Preparation of Antigen-Binding Units (Abus):

The subject Abus can be prepared by recombinant DNA technology, synthetic chemistry techniques, or a combination thereof. For instance, sequences encoding the desired components of the Abus, including VL, VH and the heterodimerization sequences are typically assembled and fragments ligated into an expression vector. These sequences may be assembled from other vectors encoding the desired protein sequence, from PCR-generated fragments using respective template nucleic acids, or by assembly of synthetic oligonucleotides encoding the desired sequences. However, all nucleic acid sequences encoding the Abus are preferably assembled by in-frame fusion of coding sequences. Flexons, described above, can be included between various components and domains in order to enhance the ability of the individual components to assume a configurations relatively independently of each other. To produce Nsc Abus, the L and H chain can be formed separately and then assembled, or assembled in vivo by an expression system for both chains. Such expression systems can be created by transfecting a suitable cell with a vector comprising separate transcribable regions for the L and H chain, or by co-transfecting the same cell with vectors for each chain.

The assembled Abus can be isolated using a variety of protein purification techniques known in the art. Generally, the Abu is isolated from culture media as secreted polypeptides, although they can be recovered from host cell lysates or bacterial periplasm, when directly produced without signal peptides. If the Abus are membrane-bound, they be solubilized by suitable detergent solutions commonly employed by artisans in the field. The recovered Abus may be further purified by salt precipitation (e.g., with ammonium sulfate), ion exchange chromatography (e.g. on a cationic or anionic exchange column run at neutral pH and eluted with step gradients of increasing ionic strength), gel filtration chromatography (including gel filtration HPLC), and chromatography on tag-affinity column, or on affinity resins such as protein A, protein G, hydroxyapatite, and anti-immunoglobulin.

Polynucleotides, Vectors, and Host Cells of the Present Invention

The invention provides various polynucleotides that encode the Abus of the invention. In one embodiment, this invention provides isolate polynucleotides that encode the subject Nsc Abus. In one aspect of this embodiment, the recombinant polynucleotide comprises a coding sequence that encodes the light-chain polypeptide of a subject Nsc Abu. In another aspect, the recombinant polynucleotide comprises a coding sequence that encodes the heavy-chain polypeptide of a Nsc Abu. In yet another aspect, the recombinant polynucleotide comprises two separate coding sequences, one of which codes for the light-chain polypeptide, and the other codes for the heavy-chain.

Nucleotide sequences corresponding to various regions of L or H chains of an existing antibody can be readily obtained and sequenced using convention techniques including but not limited to hybridization, PCR, and DNA sequencing. Hybridoma cells that produce monoclonal antibodies serve as a preferred source of antibody nucleotide sequences. A vast number of hybridoma cells producing an array of monoclonal antibodies may be obtained from public or private repositories. The largest depository agent is American Type Culture Collection, which offers a diverse collection of well-characterized hybridoma cell lines. Alternatively, antibody nucleotides can be obtained from immunized or non-immunized rodents or humans, and form organs such as spleen and peripheral blood lymphocytes. Specific techniques applicable for extracting and synthesizing antibody nucleotides are described in Orlandi et al. (1989) *Proc. Natl. Acad. Sci. U.S.A* 86: 3833–3837; Larrick et al. (1989) *Biochem. Biophys. Res. Commun.* 160:1250–1255; Sastry et al. (1989) *Proc. Nat. Acad. Sci., U.S.A.* 86: 5728–5732; and U.S. Pat. No. 5,969,108.

The antibody nucleotide sequences may also be modified, for example, by substituting the coding sequence for human heavy and light chain constant regions in place of the homologous non-human sequences. In that manner, chimeric antibodies are prepared that retain the binding specificity of the original antibody.

It is also understood that the polynucleotides embodied in the invention include those coding for functional equivalents and fragments thereof of the exemplified polypeptides. Functionally equivalent polypeptides include those that enhance, decrease or not significantly affect properties of the polypeptides encoded thereby. Functional equivalents may be polypeptides having conservative amino acid substitutions, analogs including fusions, and mutants.

Due to the degeneracy of the genetic code, there can be considerable variation in nucleotides of the L and H sequences, as well as the heterodimerization sequences suitable for construction of the polynucleotide and vectors of the present invention. Sequence variants may have modified DNA or amino acid sequences, one or more substitutions, deletions, or additions, the net effect of which is to retain the desired antigen-binding activity. For instance, various substitutions can be made in the coding region that either do not alter the amino acids encoded or result in conservative changes. These substitutions are encompassed by the present invention. Conservative amino acid substitutions include substitutions within the following groups: glycine, alanine; valine, isoleucine, leucine; aspatic acid, glutamic acid; asparagine, glutamine; serine, threonine; lysine, arginine; and phenylalanine, tyrosine. While conservative substitutions do effectively change one or more amino acid residues contained in the polypeptide to be produced, the substitutions are not expected to interfere with the antigen-binding activity of the resulting Abus to be produced. Nucleotide substitutions that do not alter the amino acid residues encoded are useful for optimizing gene expression in different systems. Suitable substitutions are known to those of skill in the art and are made, for instance, to reflect preferred codon usage in the expression systems.

Where desired, the recombinant polynucleotides may comprise heterologous sequences that facilitate detection of the expression and purification of the gene product. Examples of such sequences are known in the art and include those encoding reporter proteins such as β-galactosidase, β-lactamase, chloramphenicol acetyltransferase (CAT), luciferase, green fluorescent protein (GFP) and their derivatives. Other heterologous sequences that facilitate purification may code for epitopes such as Myc, HA (derived from influenza virus hemagglutinin), His-6, FLAG, or the Fc portion of immunoglobulin, glutathione S-transferase (GST), and maltose-binding protein (MBP).

The polynucleotides can be conjugated to a variety of chemically functional moieties described above. Commonly employed moieties include labels capable of producing a detectable signal, signal peptides, agents that enhance immunologic reactivity, agents that facilitate coupling to a solid support, vaccine carriers, bioresponse modifiers, paramagnetic labels and drugs. The moieties can be covalently linked polynucleotide recombinantly or by other means known in the art.

The polynucleotides of the invention can comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable to provide embodiments of this invention.

The polynucleotides embodied in this invention can be obtained using chemical synthesis, recombinant cloning methods, PCR, or any combination thereof. Methods of chemical polynucleotide synthesis are well known in the art and need not be described in detail herein. One of skill in the art can use the sequence data provided herein to obtain a desired polynucleotide by employing a DNA synthesizer or ordering from a commercial service.

Polynucleotides comprising a desired sequence can be inserted into a suitable vector which in turn can be introduced into a suitable host cell for replication and amplification. Accordingly, the invention encompasses a variety of vectors comprising one or more of the polynucleotides of the present invention. Also provided is a selectable library of expression vectors comprising at least one vector encoding the subject Abus.

Vectors of the present invention are generally categorized into cloning and expression vectors. Cloning vectors are useful for obtaining replicate copies of the polynucleotides they contain, or as a means of storing the polynucleotides in a depository for future recovery. Expression vectors (and host cells containing these expression vectors) can be used to obtain polypeptides produced from the polynucleotides they contain. Suitable cloning and expression vectors include any known in the art, e.g., those for use in bacterial, mammalian, yeast, insect and phage display expression systems.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., pBR322, pMB9, ColE1, pCR1, RP4, pUC18, mp18, mp19, phage DNAs (including filamentous and non-filamentous phage DNAs), and shuttle vectors such as pSA3 and pAT28. These and other cloning vectors are available from commercial vendors such as Clontech, BioRad, Stratagene, and Invitrogen.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include plasmids, viral vectors, including phagemids, adenoviruses, adeno-associated viruses, retroviruses, cosmids, etc. A number of expression vectors suitable for expression in eukaryotic cells including yeast, avian, and mammalian cells are known in the art. One example of an expression vector is pcDNA3 (Invitrogen, San Diego, Calif.), in which transcription is driven by the cytomegalovirus (CMV) early promoter/enhancer.

The vectors of the present invention generally comprises a transcriptional or translational control sequences required for expressing the Abus. Suitable transcription or translational control sequences include but are not limited to replication origin, promoter, enhancer, repressor binding regions, transcription initiation sites, ribosome binding sites, translation initiation sites, and termination sites for transcription and translation.

As used herein, a "promoter" is a DNA region capable under certain conditions of binding RNA polymerase and initiating transcription of a coding region located downstream (in the 3' direction) from the promoter. It can be constitutive or inducible. In general, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains responsible for the binding of RNA polymerase. Eukaryotic promoters will often, but not always, contain "TATA" boxes and "CAT" boxes.

The choice of promoters will largely depend on the host cells in which the vector is introduced. For animal cells, a variety of robust promoters, both viral and non-viral promoters, are known in the art. Non-limiting representative viral promoters include CMV, the early and late promoters of SV40 virus, promoters of various types of adenoviruses (e.g. adenovirus 2) and adeno-associated viruses. It is also possible, and often desirable, to utilize promoters normally associated with a desired light or heavy chain gene, provided that such control sequences are compatible with the host cell system.

Suitable promoter sequences for other eukaryotic cells include the promoters for 3-phosphoglycerate kinase, or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

For constructing vectors encoding Abus that are amenable for an in vivo screening using a two hybrid system, promoters suitable for expression of a reporter gene employed. Such a promoter when fused to the reporter gene, can direct transcription of it in the presence of appropriate molecules (i.e., proteins having transcriptional activation domains), and which, in the absence of a transcriptional activation domain, do not direct transcription of the reporter gene. Non-limiting examples of useful promoter are the yeast SPO13 promoter and the pADH1 promoter. Other useful promoters include those promoters which contain upstream repressing sequences (see, e.g., Vidal et al., 1995, *Proc. Natl. Acad. Sci. U.S.A.* 92:2370–2374) and which inhibit expression of the reporter gene in the absence of a transcriptional activation domain. The ability of a promoter to direct transcription of a reporter gene can be measured with conventional methods of assaying for gene expression (e.g., detection of the gene product or its mRNA, or detection of cell growth under conditions where expression of the reporter gene is required for growth of a cell).

Using well-known restriction and ligation techniques, appropriate transcriptional control sequences can be excised from various DNA sources and integrated in operative relationship with the intact selectable fusion genes to be expressed in accordance with the present invention.

In constructing the subject vectors, the termination sequences associated with the transgene are also inserted into the 3' end of the sequence desired to be transcribed to provide polyadenylation of the mRNA and/or transcriptional termination signal. The terminator sequence preferably contains one or more transcriptional termination sequences (such as polyadenylation sequences) and may also be lengthened by the inclusion of additional DNA sequence so as to further disrupt transcriptional read-through. Preferred terminator sequences (or termination sites) of the present invention have a gene that is followed by a transcription termination sequence, either its own termination sequence or a heterologous termination sequence. Examples of such termination sequences include stop codons coupled to various polyadenylation sequences that are known in the art, widely available, and exemplified below. Where the terminator comprises a gene, it can be advantageous to use a gene which encodes a detectable or selectable marker; thereby providing a means by which the presence and/or absence of the terminator sequence (and therefore the corresponding inactivation and/or activation of the transcription unit) can be detected and/or selected.

In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins, e.g., ampicillin, neomycyin, G418, methotrexate, etc.; (b) complement auxotrophic deficiencies; or (c) supply critical nutrients not available from complex media. The choice of the proper marker gene will depend on the host cell, and appropriate genes for different hosts are known in the art.

In a preferred embodiment, the vector is a shuttle vector, capable of replicating in at least two unrelated expression systems. In order to facilitate such replication, the vector generally contains at least two origins of replication, one effective in each expression system. Typically, shuttle vectors are capable of replicating in a eukaryotic expression system and a prokaryotic expression system. This enables detection of protein expression in the eukaryotic host (the expression cell type) and amplification of the vector in the prokaryotic host (the amplification cell type). Preferably, one origin of replication is derived from SV40 and one is derived from pBR322 although any suitable origin known in the art may be used provided it directs replication of the vector. Where the vector is a shuttle vector, the vector preferably contains at least two selectable markers, one for the expression cell type and one for the amplification cell type. Any selectable marker known in the art or those described herein may be used provided it functions in the expression system being utilized.

The vectors embodied in this invention can be obtained using recombinant cloning methods and/or by chemical synthesis. A vast number of recombinant cloning techniques such as PCR, restriction endonuclease digestion and ligation are well known in the art, and need not be described in detail herein. One of skill in the art can also use the sequence data provided herein or that in the public or proprietary databases to obtain a desired vector by any synthetic means available in the art.

Host Cells of the Present Invention:

The invention provides host cells comprising or transfected with the vectors or a library of the vectors described above. The vectors can be introduced into a suitable prokaryotic or eukaryotic cell by any of a number of appropriate means, including electroporation, microprojectile bombardment; lipofection, infection (where the vector is coupled to an infectious agent), transfection employing calcium chloride, rubidium chloride, calcium phosphate, DEAE-dextran, or other substances. The choice of the means for introducing vectors will often depend on features of the host cell.

For prokaryotes and eukaryotic microbes such as fungi or yeast cells, any of the above-mentioned methods is suitable for vector delivery. Suitable prokaryotes for this purpose include bacteria including Gram-negative and Gram-positive organisms. Representative members of this class of microorganisms are Enterobacteriaceae (e.g *E. Coli*), *Enterobacter, Erwinia, Klebsiella, Proteus, Salmonella* (e.g. *Salmonella typhimurium*), *Serratia* (e.g., *Serratia marcescans*), *Shigella, Neisseria* (e.g. *Neisseria meningitis*) as well as *Bacilli* (e.g. *Bacilli subtilis* and *Bacilli licheniformis*). Preferably, the host cell secretes minimal amounts of proteolytic fragments of the expressed Abus. Commonly employed fungi (including yeast) host cells are *S. cerevisiae, Kluyveromyces lactis* (*K. lactis*), species of *Candida* including *C. albicans* and *C. glabrata, C. maltosa, C. utilis, C. stellatoidea, C. parapsilosis, C. tropicalus, Neurospora crassas, Aspergillus nidulans, Schizosaccharomyces pombe* (*S. pombe*), *Pichia pastoris*, and *Yarowia lipolytica*.

To perform two hybrid screening method, the suitable yeast strains can be grown and maintained according to standard methods. Saccharomyces cerevisiae are particularly useful in the invention. In certain aspects of the invention, mating of two mating competent yeast cells is desired. For example, in certain methods, a hybrid protein which includes an activation domain is expressed in one mating competent cell, and a hybrid protein which includes a DNA-binding domain is expressed in a second mating competent cell. In such a case, the transcription factor is reconstituted by mating the first and second mating competent cells. As is apparent to artisans in the field, the two mating competent cells should be of compatible mating types. For example, one mating competent cell can be of the MATa mating type, and the other mating competent cell can be of the MATα mating type. It is inconsequential which hybrid protein is expressed in which cell type. A preferred yeast cell for screening Abus that is immunoreactive with a desired antigen contains a counterselectable reporter gene which is operably fused to a promoter which facilitates elimination of yeast cells expressing the counterselectable reporters independent of the specific binding of a test Abu to an antigen of interest. In addition, a yeast cell can contain, integrated into its genome, a selectable marker (e.g., HIS3) and/or a gene whose expression can be screened (e.g., lacZ).

The above-mentioned delivery methods are also suitable for introducing vectors to most of the animal cells. Preferred animal cells are vertebrate cells, preferably mammalian cells, capable of expressing exogenously introduced gene products in large quantity, e.g. at the milligram level. Non-limiting examples of preferred cells are NIH3T3 cells, COS, HeLa, and CHO cells.

The animal cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, animal cells can be grown in a defined medium that lacks serum but is supplemented with hormones, growth factors or any other factors necessary for the survival and/or growth of a particular cell type. Whereas a defined medium supporting cell survival maintains the viability, morphology, capacity to metabolize and potentially, capacity of the cell to differentiate, a defined medium promoting cell growth provides all chemicals necessary for cell proliferation or multiplication. The general parameters governing mammalian cell survival and growth in vitro are well established in the art. Physicochemical parameters which may be controlled in different cell culture systems are, e.g., pH, $PO_2$, temperature, and osmolarity. The nutritional requirements of cells are usually provided in standard media formulations developed to provide an optimal environment. Nutrients can be divided into several categories: amino acids and their derivatives, carbohydrates, sugars, fatty acids, complex lipids, nucleic acid derivatives and vitamins. Apart from nutrients for maintaining cell metabolism, most cells also require one or more hormones from at least one of the following groups:

steroids, prostaglandins, growth factors, pituitary hormones, and peptide hormones to proliferate in serum-free media (Sato, G. H., et al. in "Growth of Cells in Hormonally Defined Media," Cold Spring Harbor Press, N.Y., 1982). In addition to hormones, cells may require transport proteins such as transferrin (plasma iron transport protein), ceruloplasmin (a copper transport protein), and high-density lipoprotein (a lipid carrier) for survival and growth in vitro. The set of optimal hormones or transport proteins will vary for each cell type. Most of these hormones or transport proteins have been added exogenously or, in a rare case, a mutant cell line has been found which does not require a particular factor. Those skilled in the art will know of other factors required for maintaining a cell culture without undue experimentation.

Once introduced into a suitable host cell, expression of the Abus can be determined using any nucleic acid or protein assay known in the art. For example, the presence of transcribed mRNA of L or H chain, or the Abu can be detected and/or quantified by conventional hybridization assays (e.g. Northern blot analysis), amplification procedures (e.g. RT-PCR), SAGE (U.S. Pat. No. 5,695,937), and array-based technologies (see e.g. U.S. Pat. Nos. 5,405,783, 5,412,087 and 5,445,934), using probes complementary to any region of Abu polynucleotide.

Expression of the vector can also be determined by examining the Abu expressed. A variety of techniques are available in the art for protein analysis. They include but are not limited to radioimmunoassays, ELISA (enzyme fused immunoradiometric assays), "sandwich" immunoassays, immunoradiometric assays, in situ immunoassays (using e.g., colloidal gold, enzyme or radioisotope labels), western blot analysis, immunoprecipitation assays, immunoflourescent assays, and PAGE-SDS.

Uses of the Polynucleotides, Vectors and Host Cells of the Present Invention

The polynucleotides and vectors of this invention have several specific uses. They are useful, for example, in expression systems for the production of the subject Nsc Abus. The polynucleotides are useful as primers to effect amplification of desired polynucleotides. Furthermore, The polynucleotides of this invention are also useful in pharmaceutical compositions including vaccines, diagnostics, and drugs.

The host cells of this invention can be used, inter alia, as repositories of the subject polynucleotides, vectors, or as vehicles for producing and screening desired Abus in vivo based on their intracellular antigen binding specificities or capabilities.

Accordingly, the invention provides a method of generating a non-single-chain antigen-binding unit in a yeast cell. The method involves co-expressing in the yeast cell (a) a light (L) chain polypeptide comprising a light (L) chain variable region fused to a first leucine zipper sequence; and (b) a heavy (H) chain polypeptide comprising a heavy (H) chain variable region fused to a second leucine zipper sequence, wherein the L and H chain polypeptides dimerize to form an antigen-binding site in the yeast cell through an interaction between the first and second leucine zipper sequences.

In a separate embodiment, the present invention provides a method of identifying a non-single-chain antigen-binding unit that is immunoreactive with a desired antigen. The method comprises the steps of: (a) recombinantly co-expressing within a population of yeast cells (i) a reporter gene operably linked to a first DNA-binding-protein recognition site (DNA-BPRS); (ii) a first antigen fusion gene encoding the desired antigen fused in-frame with a first DNA-binding moiety which specifically binds to said first DNA-BPRS; (iii) a plurality of expression vectors that encodes a genetically diverse repertoire of antigen-binding units, each antigen-binding unit comprising a variable region of a first antibody chain fused to a first dimerization sequence, and a variable region of a second antibody chain fused to a second dimerization sequence and a gene activation moiety; wherein the variable regions of the first and second antibody chains dimerize to form an antigen-binding site through an interaction between the first and second leucine zipper sequences; and (b) detecting expression of said reporter gene, wherein an increase in the expression indicates a specific binding between an antigen binding fragment and the desired antigen, thereby identifying an antigen binding unit that is immunoreactive with the desired antigen.

In one aspect of this embodiment, the co-expression of a plurality of expression vectors comprises mating a first population of yeast cells that carries expression vectors encoding a repertoire comprising variable regions of a first antibody chain, with a second population of yeast cells that carries expression vectors encoding a repertoire comprising variable regions of a second antibody chain. Where desired, the screening of desired Abu may further involve the process of counter selecting yeast cells that express the reporter gene independent of the specific interaction between an antigen binding fragment and the desired antigen. Such counterselection typically involves the steps of (a) recombinantly co-expressing within the population of yeast cells (i) a counterselectable gene operably linked to a second DNA-binding protein recognition site (DNA-BPRS); (ii) a second antigen fusion gene encoding a second antigen fused in-frame with a second DNA-binding moiety which specifically binds to the second DNA-BPRS, wherein the second antigen differs structurally from the first antigen; (b) culturing the yeast cells under condition suitable for expression for the reporter gene and the counterselectable gene; and (c) detecting growth of yeast cells and expression of the reporter gene, wherein the growth of the yeast cells and an increase in the reporter gene expression indicate that a specific binding between an antigen-binding unit and the desired antigen has occurred.

The two-hybrid screening and counterselecting procedures are well established in the art, and need not be detailed herein. Briefly, the detection of specific binding of the subject Abus with their respective antigens in yeast cells can be performed using any conventional methods described in U.S. Pat. Nos. 5,283,173, 5,965,368, 5,948,620, 6,171,795, 6,132,963, 5,695,941, 6,187,535, 6,159,705, 6,057,101, 6,083,693, 5,928,868, 6,200,759, WO 95/14319, WO 95/26400).

Kits Comprising the Vectors of the Present Invention

The present invention also encompasses kits containing the vectors of this invention in suitable packaging. Kits embodied by this invention include those that allow generation of Abus reconstituted via the interaction of the first and second leucine zippers.

Each kit necessarily comprises the reagents which render the delivery of vectors into a host cell possible. The selection of reagents that facilitate delivery of the vectors may vary depending on the particular transfection or infection method used. The kits may also contain reagents useful for generating labeled polynucleotide probes or proteinaceous probes for detection of Abus. Each reagent can be supplied in a solid form or dissolved/suspended in a liquid buffer suitable for inventory storage, and later for exchange or addition into the reaction medium when the experiment is performed. Suitable packaging is provided. The kit can optionally provide additional components that are useful in the procedure. These optional components include, but are not limited to, buffers, capture reagents, developing reagents, labels, reacting surfaces, means for detection, control samples, instructions, and interpretive information.

Further illustration of the development and use of Abus, polynucleotides, vectors and host cells according to this invention are provided in the Example section below. The examples are provided as a guide to a practitioner of ordinary skill in the art, and are not meant to be limiting in any way.

EXAMPLES

Construction of Non-Single-Chain Antigen-Binding Units

The conventional yeast two hybrid system and various improved systems developed has been widely used to detect protein-protein interaction. In this system, a protein or part of protein is fused with the transcriptional factor DNA binding domain as bait, and a second protein or a cDNA library is fused at the C-terminal with a transcriptional activation domain. If the second protein or a library encoded protein interact with the bait protein, the interaction will bring the activation domain to the proximity of transcriptional machinery, where the DNA binding domain-bait fusion protein binds a upstream activation sequence that is operably linked to a reporter gene. This will result the activation of the reporter gene that can be measured or selected. The reporter gene in the yeast two hybrid system often utilize a DNA-binding domain recognition sequence that is specifically recognized by the DNA binding domain and that is linked with promoter that can drive the reporter gene expression. The two-hybrid system provides an effective approach to clone genes that associate with another protein such as proteins in signaling complex.

We have developed a strategy to genetically select antigen-binding fragment in an improved yeast two hybrid system. In one embodiment, the variable region of light chain and the variable region of heavy chain are non-covalently paired through a well-studied leucine zipper dimerization motif. In the motif, an amphipathic alpha-helix structure has the hydrophobic group face one side, while the charged group facing the other side. A leucine zipper forms an amphipathic alpha-helix in which the leucines of the motif in one molecule can protrude from the helix and interdigitate with the leucines of the zipper motif in the other protein molecule in parallel to form a coiled coil. The leucines occupy every seventh residue in the LZ (leucine zipper) motif. Four repeats were introduced in the each of the subunits or domains of antigen-binding molecules. The diversity of the antibody repertoire were generated through random recombination of two pairs.

Example 1

Functional Dimerization of Vh/Vl of Anti-Ras Antibody Y238 through Leucine Zipper Motif of Fos/Jun Protein in Yeast Cells, and Detection of Their Interaction with Ras Protein Antigen in an Improved and Modified Yeast Two Hybrid System a) Construction of Three-Vector System for Simultaneously Expressing Antigen, the Pairs of the Antibody Molecules in a Yeast/E. coli Shuttle Vectors Construction of pSF83 (pGa14DB-Ras)—PCR primers Ncras and Noras3, with the following sequence: ATGGC-CATGGTCACAGAATACAAGCTTGTGGT (SEQ ID NO. 1), and TAAGAATGCGGCCGCTCAGGACAGCACA-CATTTGC (SEQ ID NO. 2) respectively, were used to PCR amplification of ras oncogene from cDNA library. The PCR reaction was carried out under the following conditions: denaturing at 94 Co for 30", annealing at 55 for 30", 72 for 60" for 28 cycles with Pfu polymerase (Roche Molecular Biochemicals). The PCR product was purified, and digested with Nco I and Not I, that were incorporated into the primers Ncras and Noras3 respectively, and then ligated to pGBKT7 (clontech), that was also cut with Nco I and Not I. pSF83 is Kan resistance in E. coli, and contains TRP1 marker for selection in yeast.

Construction of pSF85-pHybLex/Zeo (Invitrogen) was subjected to digestion by Hind III, and the 632 bp Hind III fragment containing the LexA DNA binding domain was removed, resulting plasmid pSF74. Next, a gene fragment containing leucine zipper domain of oncoprotein Jun and cloning sites for inserting the antibody gene in-frame fused with the Jun leucine zipper was synthesized, and cloned into the Sac I and Pst site using standard molecular biology techniques known in the field (Sambrook et al., 1989. Molecular Cloning, a laboratory manual), resulting plasmid pSF86. The sequence of Sac I-Pst I fragment was listed in FIG. 1B. The vector contains Sfi I and Not I for inserting the antibody genes, either a light chain, or VL, or heavy chain, or VH downstream of the ADH1 promoter.

To establish a model system, the light chain of anti-ras antibody Y238 (Cochet et al., 1998. Molecular Immunology. 35:1097–1110) was synthesized using oligos and PCR techniques known in the fields, the assembled Y238 anti-ras antibody light chain was attached with Sfi I and Not I restriction sites at the N-terminal and C-terminal sequence respectively. The fragment was then digested with Sfi I and Not I, and ligated to above vector pSF86, cut with Sfi I and Not I, resulting plasmid pSF85 (FIG. 1). The plasmid has zeocin selection marker under dual promoters control, Pem-7 promoter for expressing the selection marker gene in E. coli and Ptefl promoter in yeast cells.

Figures 2A, 2B:
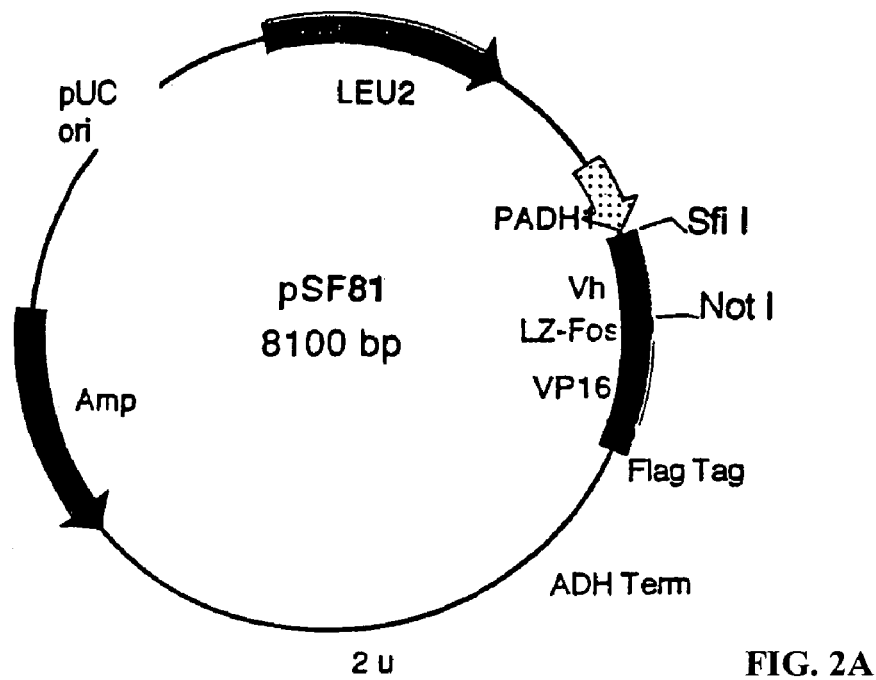
FIG. 2 is a schematic representation depicting the plasmid designated pSF81. pSF81 is a yeast shuttle vector for expressing the heavy chain or VH segment fused with Fos leucine zipper domain and VP16 activation domain tagged with FLAG (A). It contains the cloning sites Sfi I and Not I for inserting the heavy chain or VH segment (e.g. VH of the anti-Ras antibody) and the sequences for encoding the Fos leucine zipper (B).
Figure 3:
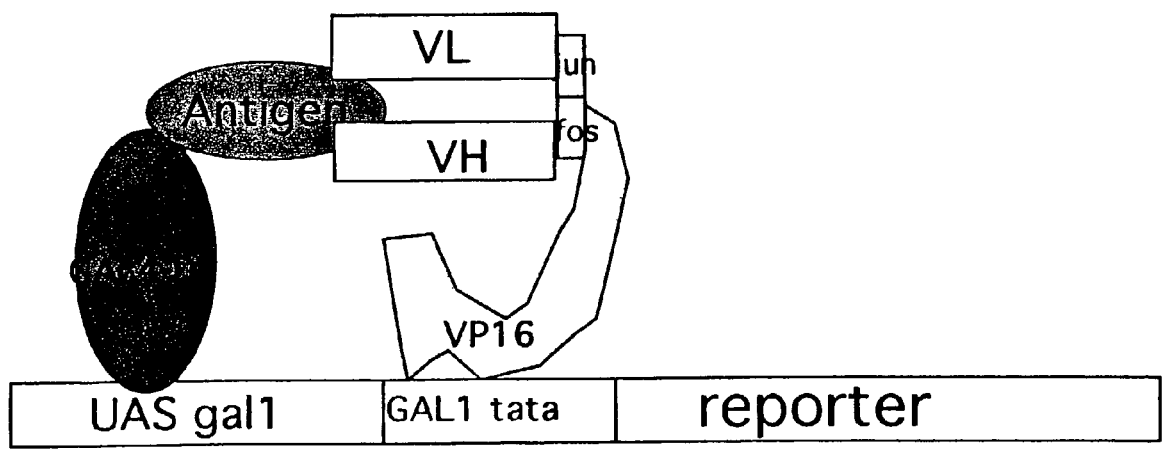
FIG. 3 depicts a principal scheme of detecting specific binding of a subject non-single-chain antigen-binding unit with its respective antigen using a yeast two hybrid system.
Figure 4:
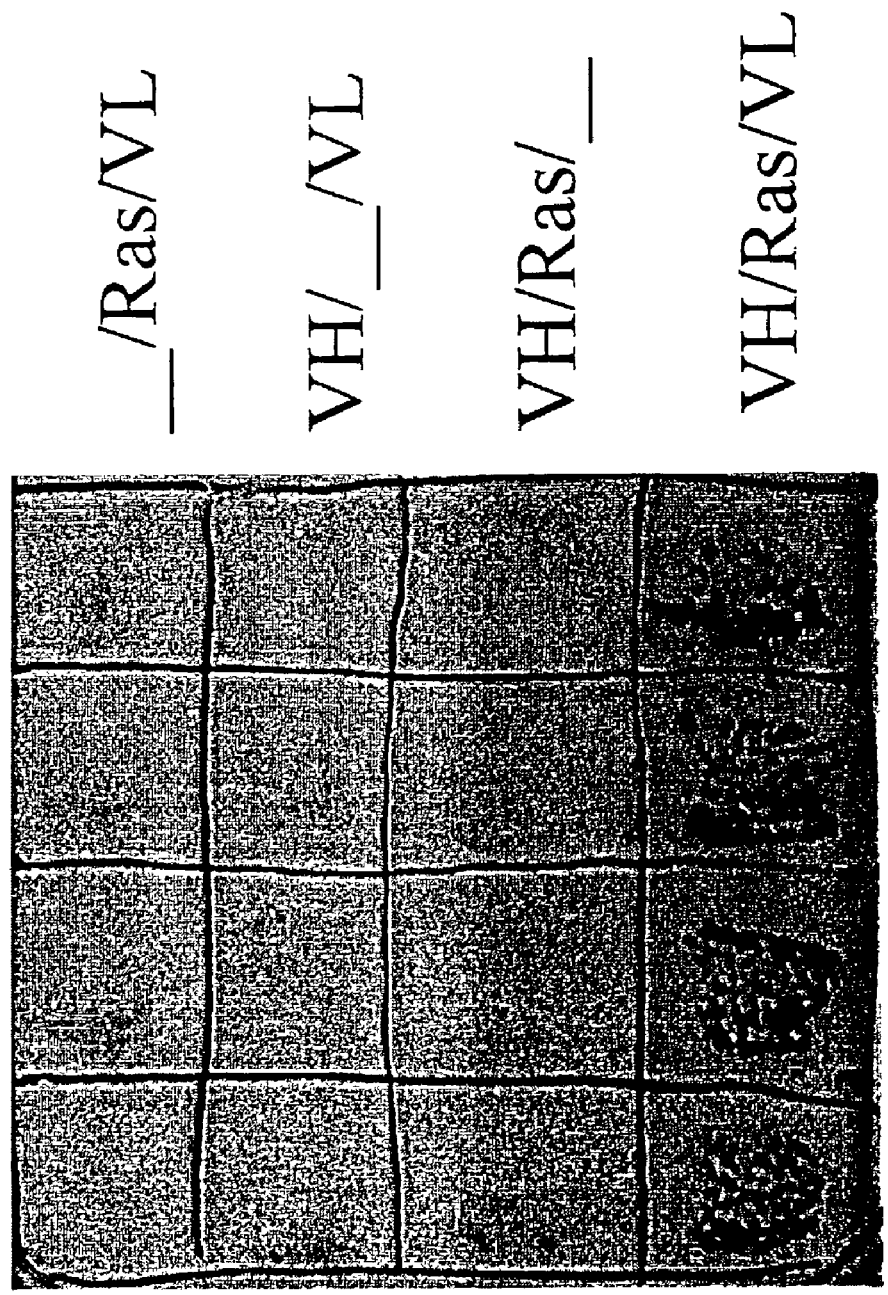
FIG. 4 depicts the specific binding between a leucine zipper stabilized, anti-Ras antigen-binding unit with its respective antigen Ras in yeast cells.
Figure 5:
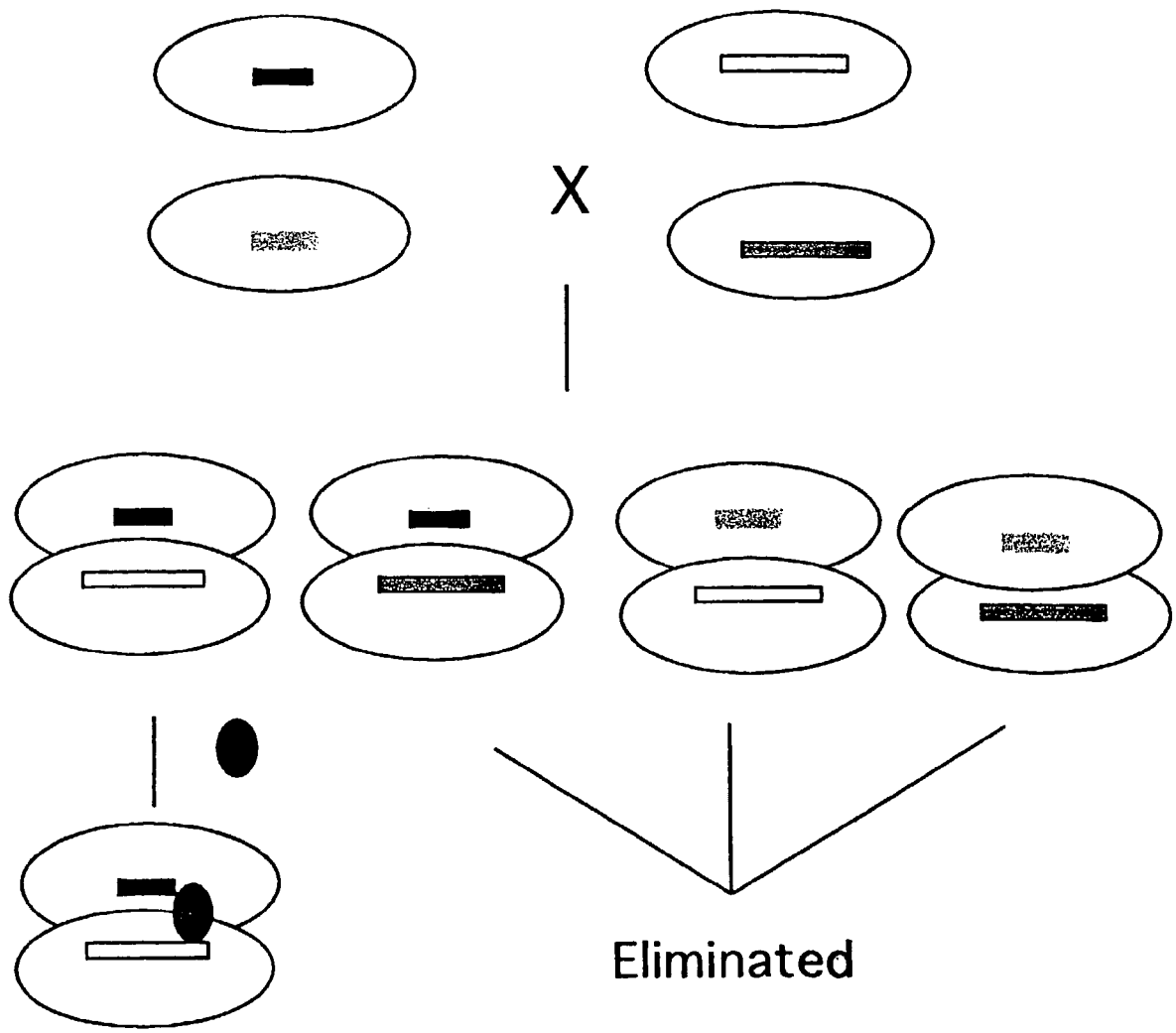
FIG. 5 shows construction of a genetically diverse repertoire of non-single-chain antigen-binding units in yeast cells by mating two different populations of yeast cells: one carries the L chain polypeptides and the other carries the H chain polypeptides.

Construction of pSF81: first, the VP16 transcriptional activation domain was synthesized using oligos and PCR assembly techniques known in the field. The NLS (nuclear localization sequence) was added at the N-terminal and the FLAG tag was added at the C-terminal of VP16 activation domain. The gene fragment was cloned into the two Hind III sites of pGADT7 vector and therefore replaced the Hind III fragment containing the Ga14 AD in the pGADT7 vector. A leucine zipper fragment of Fos from plasmid pSF72 was subsequently PCR amplified and fused upstream of the VP16 activation domain, with cloning sites Sfi I and Not I for inserting the heavy chain, (or VH, or VHCh1) of the antibody pairs, resulting plasmid pSF79. The heavy chain of anti-ras antibody Y238 (Cochet et al., 1998. Molecular Immunology. 35:1097–1110) was synthesized using oligos and PCR techniques known in the fields, the assembled Y238 anti-ras antibody heavy chain was attached with Sfi I and Not I restriction sites at the N-terminal and C-terminal sequence respectively. The fragment was then digested with Sfi I and Not I, and ligated to above vector pSF79, cut with Sfi I and Not I, resulting plasmid pSF81 (FIG. 2). This plasmid has amp marker for selection in E. coli, and Leu2 for selection in yeast.

b) Preparation of Yeast Cells Transformed with Above Expression Vectors

Competent yeast cells AH109 are prepared and transformed by pSF83 and pSF85 by Lithium Acetate methods as described (Geitz et al., 1992. Nucleic Acids Res. 20:1425), and selected on yeast drop-out media for growth in the absence of tryptophan, and presence of antibiotics zeocin at concentration 25 ug/ml. Haploid cells of the yeast saccharomyces cerevisiae exhibit either of two cellular phenotypes, the mating types α or a. these cells can reproduce by mitotic cell cycle. However, when cells of opposite mating type are co-cultured, they participate a mating process that results in cell and nuclear fusion to create an a/a diploid zygotes. Like the haploid cells, α/a diploid cells can reproduce by mitosis. Yeast mating is a convenient way to pair the plasmid expressing the heavy chain and the plasmid expressing the light chain. The AH 109 transformed with above two plasmids expressing the Y238 VL chain in pSF85 was mated with yeast cells of opposite mating type, Y187, that is transformed with pSF81, expressing the Vh part of antibody Y238 and selected for growth in the absence of Leucine. The mating can be carried out as described in the field (Guthrie, C & Fink G. R. 1991. Guide to Yeast Genetics and Molecular Biology. In *Methods in Enzymology* (Academic Press, San Diego) 194:1–932). After mating the diploid cells would be subject to selection on selective media, selecting for growth of cells that expressing the antibody-like antigen binding molecule that specifically recognize the expressed antigen in the absence of tryptophan, adenosine-hemisulfate, histidine, and in the presence of antibiotics zeocin at concentration 25 ug/ml.

c) Recovery of Antigen and Vh, Vl Expression Plasmids in *E.coli*

The DNA is prepared and isolated from yeast as described (Guthrie, C & Fink G. R. 1991. Guide to Yeast Genetics and Molecular Biology. In *Methods in Enzymology* (Academic Press, San Diego) 194:1–932), and transformed into *E. coli* strain DH5alpha. To select plasmids expressing the antigen, Vh, Vl, electroporated cells are plated on different selection plates, on Amp plate for the plasmid expressing the Vh, and kan plate for the plasmid expressing the ras, and zeocin for the plasmid expressing the Vl. Clones are further sequenced and identities of the clones are confirmed.

Example 2

Generation of Combinatorial Genetically Diverse Repertoire of Antigen Binding Fragments Through Dimerization of the Pairs of Antigen Binding Fragments Production of V domains of different specificities creates the ability for a mammal to respond to diverse antigen. The V domains are derived from many potential germ line sequences via a complex process involving recombination, mutation and selection.

PCR amplification of VH and construction VH-LZ-VP16 hybrid expression library and of VL and construction of VL-LZ library: to optimize the coverage of the diversity of the antibody genes, we take the advantage of the recent completion of human genome sequence and the catalogue of all the functional germline V genes in the database. The design of the primer pairs therefore are aimed at recognizing all the genes, or as many as possible. First, the V gene encoding the CDR1 and CDR2 from both germline or rearranged mRNA is PCR amplified using primers corresponding to the leader sequence, or the N-terminal of the domains, and the frame 3 regions of both heavy and light chain. Next, the CDR3 is amplified using the primers corresponding to the frame 3 and the J segments of both heavy and light chain. As VJ in light chain or VDJ in heavy chain DNA rearrangement in lymphocytes, the first PCR product and the second PCR product are combined through recombinant PCR or conventional molecular biology techniques known in the field, with addition of the restriction site Sfi I on the N-terminal and Not I at the C-terminal. In this way, each CDR1 and CDR2 in the V gene will recombine randomly with CDR3 in either light chain or heavy chain and increase the diversity. The recombinatory VH fragments are then digested with Sfi I and Not I, and ligated to the said vector pSF79, resulting a library of Vh-LZ-VP16 hybrid protein. The recombinatory VL library is also cut with Sfi I and Not I, and ligated to said vector pSF86, cut with Sfi I and Not I, resulting libraries of VL-LZ fusion protein.

Example 3

Screening Antigen Binding Fragment from Above Said Libraries

The process typically involves the following steps: (a) constructing plasmid expressing antigen fused with DNA binding domain: cDNA library or desired antigen protein can be fused with DNA binding domain such as Ga14 DNA binding domain in cloning vector such as pGBKT7; and (b) preparing yeast cells transformed with above expression vectors or libraries.

Competent yeast cells AH109 are prepared and co-transformed with plasmid expressing Ga14-antigen fusion in vector pGBKT7 and the above said VL-LZ library in pSF86 by Li-Ac methods as described (Geitz et al., 1992. Nucleic Acids Res. 20:1425), and selected on yeast drop-out media for growth in the absence of tryptophan, and presence of antibiotics zeocin at concentration 50 ug/ml. The AH109 transformed with above two plasmids expressing the antigen and VL-LZ fusion was mated with yeast cells of opposite mating type, Y187, that is transformed with library expressing the Vh-LZ-VP16 fusion protein and selected for growth in the absence of Leucine. The mating can be carried out as described in the field (Guthrie, C & Fink G. R. 1991. Guide to Yeast Genetics and Molecular Biology. In *Methods in Enzymology* (Academic Press, San Diego) 194:1–932). After mating the diploid cells are subject to selection on selective media, selecting for growth of cells that expressing the antigen-binding units that specifically recognize the expressed antigen in the absence of tryptophan, adenosine-hemisulfate, histidine, and in the presence of antibiotics zeocin at concentration 50 ug/ml.

Where desired, the vectors encoding the subject Abu can be recovered in *E.coli*. The DNA is prepared and isolated from yeast as described (Guthrie, C & Fink G. R. 1991. Guide to Yeast Genetics and Molecular Biology. In *Methods in Enzymology* (Academic Press, San Diego; Marcil, R. and Higgins, D. R. 1992.Nucleic Acids Res. 20:917), and transformed into *E. coli* strain DH5alpha. To select plasmids expressing the antigen, Vh, Vl, electroporated cells are plated on different selection plates, on Amp plate for the plasmid expressing the Vh, and kan plate for the plasmid expressing the antigen in the pGBKT7 vector, and zeocin for the plasmid expressing the Vl. Clones can be further sequenced and identities of the clones can be confirmed.

Example 4

Construction of Host Strain that Counterselect Non-Specific Antigen-Binding Units A host strain capable of counterselecting non-specific Abus can be generated as follows. It has been previously characterized that the cyh2 gene encodes the L29 ribosome subunit. Cycloheximide blocks polypeptide elongation during translation and prevents cell growth. However, a cycloheximide resistance allele cyh2r was identified (Kaufer et al. (1983) *Nucleic Acids Res.* 11:3123) due to a single amino acid change in the cyh2 protein. The sensitivity of the wild type cyh2 protein to the drug is dominant and thus the cells expressing both the wild-type and mutant cyh2 protein fail to grow on media containing cycloheximide. In this counterselection scheme, the endogenous cyh2 gene is replaced with the mutant allele cyh2r. The wild-type cyh2 is introduced as transgene under the control of a LexA binding site (LexA operation sequence). In this same host strain, LexA DNA binding domain is fused with an unrelated antigen, which may be expressed from a chromosome location or plasmid. If the selected antigen-binding unit is non-specific to an antigen of interest (i.e. it also binds to the unrelated antigen), then the VP16 activation domain will be brought to proximity to the LexA binding site and drive the expression of counterselectable reporter cyh2. As a result, cells expressing cyh2 are killed in the presence of cycloheximide, thus facilitating a specific selection of those cells expressing antigen-binding units specifically binding to the desired antigen. Aside from cyh2, SUP4-o and CAN1 can also be used as the counterselectable marker.

What is claimed is:

1. A method of identifying a non-single-chain antigen-binding unit that is immunoreactive with a desired antigen in a yeast cell, comprising:
   (a) recombinantly co-expressing within a population of yeast cells
      (i) a reporter gene operably linked to a first DNA-binding-protein recognition site (DNA-BPRS);
      (ii) a first antigen fusion gene encoding the desired antigen fused in-frame with a first DNA-binding moiety which specifically binds to said first DNA-BPRS;
      (iii) a plurality of expression vectors that encodes a genetically diverse repertoire of non-single-chain antigen-binding units, each antigen-binding unit comprising a variable region of a first antibody chain fused to a first dimerization sequence, and a variable region of a second antibody chain fused to a second dimerization sequence and a gene activation moiety; wherein the variable regions of the first and second antibody chains dimerize through an interaction between the first and second dimerization sequences to form the antigen-binding unit; and
   (b) detecting expression of said reporter gene, wherein an increase in the expression indicates a specific binding between the antigen-binding unit and the desired antigen, thereby identifying an antigen-binding unit that is immunoreactive with the desired antigen.

2. The method of claim 1, wherein the first antibody chain is light chain, and the second antibody chain is heavy chain.

3. The method of claim 1, wherein the first antibody chain is heavy chain, and the second antibody chain is light chain.

4. The method of claim 1, wherein the first dimerization sequence is Fos leucine zipper and the second dimerization sequence is Jun leucine zipper.

5. The method of claim 1, wherein the first dimerization sequence is Jun leucine zipper and the second dimerization sequence is Fos leucine zipper.

6. The method of claim 1, wherein co-expression of a plurality of expression vectors comprises mating a first population of yeast cells that carries expression vectors encoding a repertoire comprising variable regions of a first antibody chain, with a second population of yeast cells that carries expression vectors encoding a repertoire comprising variable regions of a second antibody chain.

7. The method of claim 1, further comprising the step of counter selecting yeast cells that express the reporter gene independent of the specific interaction between an antigen binding fragment and the desired antigen.

8. The method of claim 7 wherein the step of counter selecting further comprising:
   (a) recombinantly co-expressing within the population of yeast cells
      (i) a counterselectable gene operably linked to a second DNA-binding protein recognition site (DNA-BPRS);
      (ii) a second antigen fusion gene encoding a second antigen fused in-frame with a second DNA-binding moiety which specifically binds to the second DNA-BPRS, wherein the second antigen differs structurally from the first antigen;
   (b) culturing the yeast cells under condition suitable for expression for the reporter gene and the counterselectable gene; and
   (c) detecting growth of yeast cells and expression of the reporter gene, wherein an increase in the reporter gene expression in the absence of an increase in the counterselectable gene expression indicates that a specific binding between an antigen-binding unit and the desired antigen has occurred.

9. The method of claim 1, wherein the reporter gene is selected from the group consisting of LEU2, TRP1, HIS3, LacZ, URA3, and MEL.

10. The method of claim 1, wherein said DNA-binding-protein recognition site comprises at least one binding site for a protein selected from the group consisting of GAL4, LexA, and Ace1.

11. The method of claim 1, wherein said DNA-binding moiety comprises the DNA-binding domain of a protein selected from the group consisting of GAL4, LexA, and Ace1.

12. The method of claim 1, wherein said gene activating moiety comprises the transcription activation domain selected from the group consisting of GAL4 and VP16.

13. The method of claim 8, wherein said counterselectable gene is selected from the group consisting of URA3, LYS5, GAL1, CYH2, and CAN1.

14. The method of claim 13, wherein said counterselectable gene is integrated into the genome of the population of mating or mated yeast cells.

15. The method of claim 13, wherein said expression of said counterselectable gene is lethal to a yeast cell.

* * * * *